United States Patent
Jackson et al.

(10) Patent No.: US 6,753,151 B1
(45) Date of Patent: Jun. 22, 2004

(54) INTERACTIONS OF KU POLYPEPTIDES AND APPLICATIONS THEREOF

(75) Inventors: Stephen P. Jackson, Cambridge (GB); David A. Gell, North Yorkshire (GB)

(73) Assignee: Kudos Pharmaceuticals Limited, Cambridge (GB)

( * ) Notice: Subject to any disclaimer, the term of this patent is extended or adjusted under 35 U.S.C. 154(b) by 0 days.

(21) Appl. No.: 09/569,037

(22) Filed: May 11, 2000

Related U.S. Application Data

(63) Continuation-in-part of application No. PCT/GB00/01245, filed on Mar. 31, 2000.

(30) Foreign Application Priority Data

Apr. 1, 1999 (GB) .............................................. 9907687

(51) Int. Cl.[7] .............................................. G01N 33/53
(52) U.S. Cl. ........................... 435/7.1; 435/4; 435/7.31; 530/300; 530/327
(58) Field of Search ................................ 530/300, 327; 435/4, 7.1, 7.2, 7.31

(56) References Cited

U.S. PATENT DOCUMENTS 5,989,808 A  * 11/1999  Young et al. .................. 435/6
6,242,175 B1 * 6/2001 Jackson et al. ................ 435/5

FOREIGN PATENT DOCUMENTS

| GB | 2321702    | * 5/1998 |
| WO | WO 98/05763 | 2/1998 |
| WO | WO 00/00644 | 1/2000 |
| WO | WO 00/12716 | 3/2000 |

OTHER PUBLICATIONS

Berendsen HJC. A glimpse of the holy grail? Oct. 23, 1998. Science 282: 642–643.*
Wu et al, "Protein–Protein and Protein–DNA Interaction Regions within the DNA End–Binding Protein Ku70–Ku86", Molecular and Cellular Biology 16(9):5186–5193 (1996).
Gell and Jackson, "Mapping of protein–protein interactions within the DNA–dependent protein kinase complex", Nucleic Acids Research 27(17):3494–3502 (1999).

* cited by examiner

Primary Examiner—James Ketter
Assistant Examiner—David Lambertson
(74) Attorney, Agent, or Firm—Nixon & Vanderhye P.C.

(57) ABSTRACT

Ku is a protein found in a wide range of organisms. It comprises two tightly-associated subunits termed Ku70 and Ku80. The present invention relates to the discovery and characterisation of an interaction between Ku70 and Ku80 and DNA-$PK_{CS}$. Various applications based on this interaction are provided. These are relevant to numerous cellular processes which are of interest in therapeutic contexts.

10 Claims, 6 Drawing Sheets

| Construct | Amino Acids |
|---|---|
| Ku80 | 1-732 |
| Ku80ΔN1 | 338-732 |
| Ku80ΔN2 | 418-732 |
| Ku80ΔN4 | 473-732 |
| Ku80ΔN5 | 524-732 |
| Ku80ΔN6 | 595-732 |
| Ku80ΔN7 | 663-732 |
| Ku80ΔN8 | 710-732 |
| Ku80ΔC1 | 1-704 |
| Ku80ΔC2 | 1-662 |
| Ku80ΔC3 | 1-592 |
| Ku80ΔC4 | 1-530 |
| Ku80ΔC5 | 1-465 |

Figure 5

|  | Peptide |
|---|---|
| EEAKKFLAPKDKPSGDTAAVFEEGGDVDDLLDMI | |
| EEAKKFLAPKDK | A |
| LAPKDKPSGDTA | B |
| PSGDTAAVFEEG | C |
| AVFEEGGDVDDL | D |
| EGGDVDDLLDMI | E |

FIGURE 6

```
                                                                                           DNA-PKcs
                                                                                          Interaction
                                                                                            Region
H. sapiens   663  FNNFLKALQEKVEIKQLNHFW.EIVVQDGITLITKEASGSSVTREEAKKFLAPKDKPSGDTRAVEEEGGDVDDLLDMI
C. griseus   656  FNSFLEALREKVEIIKQLNEFW.EIVVQDGVTLITKDEGSGSSVTTEEAKKFLAPKDKAKEDAAGL.EEGGDVDDLLDMI
M. musculus  655  FNSFLEALREKVEIKQLNRFW.EIVVQDGVTLITKDEATGSSITAEEAKKFLAPKDKAKEDTTGP.EEAGDVDDLLDMI
```

INTERACTIONS OF KU POLYPEPTIDES AND APPLICATIONS THEREOF

This is a continuation-in-part of PCT application No. PCT/GB00/01245, filed Mar. 31, 2000, the entire content of which is hereby incorporated by reference in this application.

The present invention relates to assays, screening methods, peptides, mimetics, and methods of use based on the discovery and characterisation of an interaction between Ku70 and Ku80 and DNA-PK$_{cs}$. More particularly, aspects of the invention are based around peptide fragments of Ku70 and Ku80. The invention relates to numerous cellular processes which are of interest in therapeutic contexts.

Ku is a protein that is found in a wide range of organisms, ranging from *Saccharomyces cerevisiae* to man (Dynan and Yoo, 1998). It is expressed in all human tissues examined. Ku comprises two tightly-associated subunits of about 69 kDa and about 83 kDa. These are termed Ku70 and Ku80 (or Ku86), respectively. Although some information has been obtained regarding the regions of the Ku polypeptides that interact with one another (Cary et al., 1998; Jin and Weaver, 1997; Koike et al., 1998; Osipovich et al., 1997; Wang et al., 1998a; Wang et al., 1998b; Wu and Lieber, 1996), little is known about the precise sites of interaction and the molecular mechanism underlying it.

The most highly characterised function of Ku at the biochemical level is its ability to bind avidly to certain disruptions of the DNA double helix in a sequence independent fashion. The most well studied example of such a disruption is the DNA double-strand break (DSB; Blier et al., 1993; Devries et al., 1989; Mimori and Hardin, 1986). Other discontinuities that are recognised by Ku include single-strand breaks in the sugar-phosphate backbone of double-stranded DNA (dsDNA), and DNA single-strand to double-strand transitions, such as those that occur in hairpin loops or single-stranded gaps in a dsDNA molecule (Blier et al., 1993; Falzon et al., 1993). Once bound to a dsDNA end, Ku can move to internal positions in the DNA in an ATP-independent fashion (Paillard and Strauss, 1991; Devries et al., 1989). Ku has also been reported to be capable of sequence-specific DNA interactions (Giffin et al., 1996): for a review see (Dynan and Yoo, 1998). It has also been reported that Ku70 and possibly Ku80 are capable of interacting with DNA in the absence of their heterodimerisation partner (Chou et al., 1992; Wang et al., 1994). It has also been demonstrated that Ku heterodimers bound to DNA are able to specifically associate with one another (Cary et al., 1997).

When complexed with DNA, Ku can interact with an approximately 460 kDa polypeptide, the DNA-dependent protein kinase catalytic subunit (DNA-PKcs). DNA-PKcs is a member of the PI 3-kinase-like (PIKL) protein kinase family (Hartley et al., 1995) and, together with Ku and DNA, forms a catalytically active DNA-PK complex with Ser/Thr kinase activity (Dvir et al., 1992; Gottlieb and Jackson, 1993; Suwa et al., 1994).

Little is currently known about how Ku interacts with DNA-PKcs, although the fact that it is apparently unable to bind DNA-PKcs in the absence of DNA (Suwa et al., 1994) suggests that DNA binding by Ku induces a conformational change that permits the DNA-PKcs interaction. In particular, previous studies have provided little information about the regions of the Ku heterodimer which are involved in the DNA-PK$_{cs}$ interaction.

It has been shown that, under certain conditions, DNA-PKcs can bind to dsDNA ends and become activated in the absence of Ku (Hammarsten and Chu, 1998; Yaneva et al., 1997). Thus, whilst allosteric activation of DNA-PKcs by Ku might occur, it appears that direct interactions between DNA-PKcs and DNA can be sufficient to activate the kinase in vitro. This suggests that contacts between DNA-PKcs and DNA play an important role in DNA-PK activation, even in the presence of Ku.

A breakthrough in the understanding of DNA-PKcs/Ku function came with the discovery that defects in these proteins are associated with a subset of mutant mammalian cell lines that are defective in DNA DSB rejoining, and are profoundly sensitive to ionising radiation and other agents that generate DNA DSBs as their principal lethal lesion (Jackson, S. P., et al (1995) TIBS 20, 412–415; Critchlow, S. E., et al (1998) TIBS 23, 394–398). Indeed, the mutant phenotypes of these cells are corrected by the introduction of the appropriate Ku or DNA-PKcs expression vector, and recent work using extracts of mammalian or *Xenopus laevis* cells has provided evidence for a direct involvement of Ku and DNA-PKcs in DNA DSB rejoining (Baumann and West, 1998; Labhart, P., (1999) Mol. Cell. Biol. 19, 2585–2593). Furthermore, DNA-PK catalytic activity has been implicated at an early stage of DNA DSB repair in Xenopus cell-free extracts (Gu et al., 1996; Gu et al., 1998) and for radiation-induced DNA repair in cultured human cells (Okayasu, R., et al (1998) Radiat. Res. 149, 440–445). Coupled with the fact that Ku displays a very high affinity for dsDNA ends in vitro, these data suggest that DNA-PK functions directly in the recognition and resolution of radiation-induced DNA DSBs in vivo.

Cells deficient in DNA-PKcs, Ku80, or Ku70 are also severely impaired in V(D)J recombination, a site-specific genomic rearrangement process that takes place in the developing vertebrate immune system to help generate the vast antigen recognition capacity of antibody and T-cell receptor molecules (Jackson, S. P., et al (1995) TIBS 20, 412–415; Critchlow, S. E., et al (1998) TIBS 23, 394–398). This process requires the production of DNA DSBs between the recombining gene segments by the RAG1/RAG2 proteins (Jackson, S. P., et al (1995) TIBS 20, 412–415; Critchlow, S. E., et al (1998) TIBS 23, 394–398) and the subsequent rejoining of the DNA ends via DNA-PK-dependent mechanisms. For a single DNA rearrangement between two coding segments (V, D, or J regions) to occur, a join between the two coding sequences (known as the coding join) and one between the two non-coding signal ends (the signal join) are made. Interestingly, Ku is essential for both types of join, whereas DNA-PKcs appears to be required only for coding joins and plays a non-essential and variable role in the generation of signal joins (Bogue et al., 1998). This suggests that, at least for the repair of a sub-set of DNA DSBs, Ku is able to function in the absence of DNA-PKcs.

Consistent with the Ku-associated DNA DSB repair pathway being highly conserved throughout eukaryotic evolution, Ku is found in *S. cerevisiae* and is essential for repair of DNA DSBs by the pathway of non homologous end-joining (Boulton and Jackson, 1996b; Siede et al., 1996 and see Critchlow and Jackson, 1998 for review). Perhaps surprisingly there is no clear orthologue of DNA-PKcs encoded by the fully-sequenced *S. cerevisiae* genome. Thus, in yeast, Ku carries out DNA-repair functions independently of DNA-PK. Although it is possible that the functions of mammalian DNA-PKcs are assumed by other members of the PIKL protein kinase familly, such as Mec1p and/or Tel1p, there is no evidence to suggest that these interact physically or genetically with Ku.

Interestingly, *S. cerevisiae* Ku has also been shown to play important roles in telomere length maintenance, and in the transcriptional silencing of genes placed close to telomeric DNA (Boulton and Jackson, 1996a; Boulton and Jackson, 1998 Porter et al., 1996).

The present inventors have investigated interactions between Ku70 and Ku80, and between the two Ku subunits and DNA-PKcs. The data presented herein lead to the conclusion that the two Ku subunits are structurally and functionally related to each other, and appear to associate via a pseudo-homodimerisation mechanism. Furthermore, the work demonstrates that the extreme C-terminus of Ku80 plays an important role in the interaction between Ku and DNA-PKcs. These results provide for modulation of the structure and physiological functions of DNA-PKcs and Ku, for instance by means of peptides corresponding to conserved regions in Ku70 or Ku80 and/or regions of interaction between Ku70 and Ku80 and/or other molecules such as DNA-PKcs, and allow for postulation of a model for the evolution of the DNA-PK complex.

Based on the experimental work and discussion herein the invention is further concerned with assays and methods for identifying homologues and orthologues of Ku polypeptides.

The present inventors have analysed the amino acid sequences of Ku70 and Ku80 polypeptides from a diverse range of species, and have identified six regions of sequence homology between them. These regions are referred to as Homology regions 1–6 (HRs 1–6) and are shown in FIG. 1 as shaded boxes. Corresponding regions from other sequences, e.g. from mammalian, e.g. rodent, e.g. mouse, hamster, sequences are easily identifiable by those skilled in the art using the work, discussion and Figures presented herein. References to, and accession numbers of certain Ku70 and Ku80 sequences are provided in Table 1. Corresponding regions from the mouse sequences are provided in Table 2.

In one aspect the invention provides a peptide or polypeptide consisting of any of the amino acid sequences of any of the Homology Regions shown in FIG. 1, or a peptide or polypeptide consisting of a variant of such a sequence. Variants are discussed elsewhere herein. Variants include corresponding sequences from other animals, e.g. from mammals, e.g. from rodents. Examples of variants are the amino acid sequences of the Homology regions of mouse and hamster Ku70 or Ku80 sequences. The homology regions of the mouse sequences are provided in Table 2.

Variants of the sequences of the Homolgy Regions of human Ku70 and human Ku80 include the following: for Ku70 HR3, sequences which lack one or more residues corresponding to L420, D421, D422; for Ku80 HR3, sequences which lack one or more residues corresponding to N415, Y416, E417; for Ku70 HR5, sequences which lack one or more residues corresponding to T449, E450, K451, I452; for Ku80 HR5 sequences which lack one or more residues corresponding to S441, K442; for Ku70 HR6, sequences which lack one or more residues corresponding to E501, Q502; for Ku80 HR6 sequences which comprise one or more residues corresponding to L505, P506.

A peptide or polypeptide consisting of any of the amino acid sequences of any of the Homology Regions shown in FIG. 1 or a peptide or polypeptide consisting of a variant of such a sequence, (a "Ku Homology Region Peptide"), may be used to establish antibodies which in turn may be used in the identification of Ku polypeptides, or in the determination of the presence and/or quantity of Ku polypeptide in a test sample. Such antibodies form a further aspect of the invention in their own right. Methods of generating such antibodies, e.g. by raising them in a host organism or selection from an immunoglobulin expression libraray, are discussed elsewhere herein, and are well known to those having skill in the art.

By way of example, antibodies which bind to peptides or polypeptides consisting of any of the amino acid sequences of Ku Homology Region Peptide may be used to probe samples or expression libraries for Ku polypeptides, e.g. for the Ku polypeptide used in their generation, or for a cross-reactive Ku polypeptide. Binding of antibodies to Ku polypeptide may be determined by any method known to those skilled in the art. Methods for determining binding and interaction are discussed herein. Samples may be tissue or cellular (e.g. nuclear) extracts, or in vitro translation systems expressing nucleic acids of interest. Expression libraries may be bacterial or phage libraries.

Methods of determining the presence of, and optionally quantifying the amount of a Ku polypeptide in a test sample may have a diagnostic purpose, e.g. in the diagnosis of any medical condition discussed herein (e.g. in a disease or disorder associated with loss of a Ku polypeptide). Such methods may also be used to evaluate a therapy to treat such a condition.

Ku Homology Region Peptides as defined herein correspond to regions of Ku that are important for Ku function, e.g. for binding to proteins or nucleic acid, or for maintaining tertiary structure. Accordingly, they may interact with other molecules and may be used to disrupt interaction between Ku and such other molecules. For instance a peptide corresponding to HR5 or HR6 may be used to interfere with interaction between Ku70 and Ku80, with functional or biological consequences as discussed. Similarly, a peptide corresponding to any of HR1, HR2, HR3 or HR4 may be used to modulate a Ku-dependent activity or function which may have biological and/or therapeutic consequences.

In various further aspects, the present invention provides for nucleic acid encoding a polypeptide consisting of a Ku Homology Region Peptide, for vectors containing such nucleic acid, and for host cells containing such nucleic acid or such vectors. Nucleic acids, vectors and host cells are discussed further elsewhere herein, and are useful in production of peptides and polypeptides by recombinant means.

Further peptides of interest in the present invention correspond to the region of Ku80 identified herein as being necessary and sufficient for binding to DNA-PKCS, and may include or consist of the amino acid sequence EGGDVDDLLDMI (SEQ ID NO:1). Aspects of the invention based on this include assay methods for determining binding between Ku80 or EGGDVDDLLDMI (SEQ ID NO:1) on the one hand and DNA-PKCS on the other, identification of binding partners, and assay methods for agents that modulate, especially disrupt, such binding and which have therapeutic potential.

As used herein, the term "EGGDVDDLLDMI peptide" refers to a peptide which comprises or consists of the amino acid sequence EGGDVDDLLDMI (SEQ ID NO:1) and which has the ability to bind DNA-$PK_{CS}$. The term also refers to which comprise a variant of the sequence amino acid sequence EGGDVDDLLDMI (SEQ ID NO:1) and which have the ability to bind DNA-$PK_{CS}$. Variants are discussed elsewhere herein. Variants of the amino acid sequence EGGDVDDLLDMI (SEQ ID NO:1) include the corresponding regions of the related sequences shown in FIG. 6 (SEQ ID NOS:16–18) (multiple sequence alignment generated using the program "pileup" from the sequence analysis "Wisconsin Package, version 8.1" (Program Manual for the Wisconsin Package, Version 8, September 1994, Genetics Computer Group: Gap creation 3.00; Gap extension 0.10).

EGGDVDDLLDMI peptides may for example be: (i) the amino acid sequence EGGDVDDLLDMI (SEQ ID NO:1) or a variant thereof; or (ii) the peptide of (i) fused to a heterologous amino acid sequence (see below), i.e. a sequence to which it is not naturally fused in Ku80, or (iii) the peptide of (i) fused to a sequence with which it is naturally fused in wild-type Ku80, but in a peptide or polypeptide which has the ability to bind to DNA-PK$_{CS}$.

A peptide in accordance with any aspect of the present invention may include one or more heterologous amino acids joined to the specified peptide. By "heterologous" is meant not occurring in a Ku80 or Ku70 polypeptide joined by a peptide bond without intervening amino acids to the relevant specified peptide, that is to say usually a chain of amino acids which is not found naturally joined to the specified peptide at the position of fusion in the peptide of the invention. Usually where heterologous amino acids are included, the contiguous sequence of amino acids does not occur within Ku70 and/or Ku80, and may include or be 5 or more, preferably 10 or more, more preferably 15 or more, 20 or more or 30 or more amino acids with a sequence which does not occur contiguously in Ku70 and/or Ku80

A peptide or polypeptide according to the invention may be about 12, 13, 14, 15, 16, 17, 18, 19, 20, 21, 22, 23–25, 25–30, 30–35, 35–40, 40–45, 45–50, 50–60, 60–70, 70–80, 80–90, 90–100, 100–125, 125–150, 150–175, 175–200, 200–250, 250–300, 350–400, 400–450 amino acids in length. It may be about 22 amino acids or less, 69 amino acids or less, 137 amino acids or less, 208 amino acids or less, 259 amino acids or less, 314 amino acids or less, 394 amino acids or less in length. A EGGDVDDLLDMI peptide of the invention is able to bind DNA-PK$_{cs}$ and will be able to bind "DNA-PK$_{cs}$-like polypeptides", meaning not only the human DNA-dependent protein kinase catalytic subunit DNA-PK$_{cs}$ and its homologues and orthologues in other species, for example in mouse, horse, or *Xenopus laevis*, but also variants of those DNA-PK$_{cs}$ polypeptides, and polypeptides comprising an amino acid sequence which shares at least 30% amino acid sequence homology with the amino acid sequence of human DNA-PK$_{cs}$ or a homologue or orthologue thereof, more preferably at least 35% sequence homology, more preferably at least 40% sequence homology, more preferably at least 50% sequence homology, more preferably at least 70% sequence homology, more preferably at least 80% sequence homology, still more preferably at least 90% sequence homology with the amino acid sequence of human DNA-PK$_{cs}$ or a homologue or orthologue thereof. The amino acid sequence of human DNA-PK$_{cs}$ is disclosed in Dynan and Yoo, 1998 and has the database accession number U47077. Sequence homology is defined elsewhere herein. The term DNA-PK$_{cs}$-like polypeptide may be used therefore to refer to related enzymes, e.g. other kinases of the PIKL family, e.g. ATM, ATR, FRAP. The term "DNA-PK$_{CS}$-like polypeptide" also encompasses alleles, mutants, derivatives and fragments of human DNA-PK$_{cs}$ or a homologue or orthologue thereof.

Aspects of the present invention provide for the use of a peptide, whether a Ku Homology Region Peptide or an EGGDVDDLLDMI peptide or polypeptide, in screening or searching for and/or obtaining/identifying a binding partner, such as for an EGGDVDDLLDMI peptide a DNA-PK$_{cs}$-like polypeptide which has the ability to bind to said EGGDVDDLLDMI.

Thus, a further aspect of the invention provides a screening or assay method for identifying an agent which binds to a peptide of the invention, or for determining binding of an peptide of the invention to an agent of interest may include:
(a) bringing a test substance into contact with said peptide; and
(b) determining binding of the test substance to said peptide.

In one embodiment, a screening or assay method for identifying an agent which binds to an EGGDVDDLLDMI peptide, or for determining binding of an EGGDVDDLLDMI peptide to an agent of interest may include:
(a) bringing a test substance into contact with said EGGDVDDLLDMI peptide; and
(b) determining binding of the test substance to said EGGDVDDLLDMI polypeptide.

A test substance which proves to be an agent which binds to an EGGDVDDLLDMI peptide may be, for example, a DNA-PKCS-like polypeptide or an antibody.

In other embodiments the peptide is a Ku Homology Region Peptide, as disclosed.

The invention may be used to identify one or more regions of a polypeptide or other substance involved in an in vivo or an in vitro interaction with a region of Ku70 or Ku80 corresponding to a Homology Region as disclosed or the sequence EGGDVDDLLDMI (SEQ ID NO:1). This may involve identifying sequence motif(s) in a polypeptide which is/are involved in the interaction of polypeptide with the relevant amino acid sequence in Ku80 or Ku70. Various fragments of a DNA-PK$_{CS}$-like polypeptide may be used in the above assays, e.g. fragments generated by N-terminal and/or C-terminal deletions of the full DNA-PK$_{CS}$-like polypeptide sequence.

Related aspects of the present invention provide the use of an peptide sequence of the invention for determining the presence in a test sample of a binding partner which has the ability to bind to said sequence, and the use of an agent which binds a peptide of the invention for determining the presence in a test sample of a Ku70 or Ku80 peptide or polypeptide, such as an EGGDVDDLLDMI polypeptide.

A method for determining the presence in a test sample of an agent, e.g. polypeptide such as an antibody, which has the ability to bind to a peptide of the invention, may include:
(a) bringing a peptide of the invention into contact with the test sample; and
(b) determining binding of the peptide to an agent if present in the test sample.

A method for determining the presence in a test sample of a peptide of the invention, may include:
(a) bringing the an agent, e.g. polypeptide such as an antibody, into contact with the test sample; and
(b) determining binding of the agent to a substance in the test sample.

A method for determining the presence in a test sample of any agent or substance may include quantifying the amount of the agent or substance in the sample.

Methods of determining the presence of an agent or substance in a test sample may have a diagnostic purpose, e.g. in the diagnosis of any medical condition discussed herein (e.g. in a disease or disorder associated with reduction or loss of a Ku-dependent function or biological activity). Such methods may also be used to evaluate a therapy to treat such a condition.

Methods of determining binding and/or interaction in any method described herein are discussed below.

A test agent or substance employed in accordance with the present invention may be a natural or synthetic chemical compound.

A test agent or substance may be 0.005–0.01% pure, 0.01–0.05% pure, 0.05%–0.1% pure, 0.1–0.5% pure, 0.5–1% pure, 1–5% pure. pure, 5–10% pure, 10–20% pure, 20–30% pure, 30–40% pure, 40–50% pure, 50–60% pure, 60–70% pure, 70–80% pure, 80–90% pure, 90–95% pure, or substantially pure.

A screening or assay method may include purifying and/or isolating a test substance and/or substance of interest from a mixture or extract, i.e. reducing the content of at least one component of the mixture or extract, e.g. a component with which the test substance or substance of interest is naturally associated. The screening or assay method may include determining the ability of one or more fractions of a test mixture or extract to bind to peptide of the invention. The purifying and/or isolating may employ any method known to those skilled in the art.

The precise format of any of the screening or assay methods of the present invention may be varied by those of skill in the art using routine skill and knowledge. The skilled person is well aware of the need to employ appropriate control experiments.

A peptide of the invention and any agent identified by any one of the methods provided by the present invention may be isolated and/or purified and/or further investigated and/or manufactured. Various methods and uses of such compounds are discussed elsewhere herein.

The inventors have identified a number of EGGDVD-DLLDMI polypeptides which can bind to human DNA-PK$_{cs}$. These sequences form the basis of further aspects of the present invention.

Accordingly, the invention provides the EGGDVDDLL-DMI polypeptides Ku80ΔN1, Ku80ΔN2, Ku80ΔN4, Ku80ΔN5, Ku80ΔN6, Ku80ΔN7, Ku80ΔN8 as shown in FIG. 2 and variants thereof that retain ability to bind to a DNA-PK$_{cs}$-like polypeptide.

As used herein, variants of a stated amino acid sequence may have an amino acid sequence which shares at least about 30%, or 40%, or 50%, or 60%, or 70%, or 75%, or 80%, or 85%, 90% or 95% homology with the stated sequence. Homology is defined elsewhere herein.

A variant may differ by one or more amino acid residues from the stated sequence, by one or more of addition, insertion, deletion and substitution of one or more amino acid residues. It may include 1, 2, 3, 4, 5, or greater than 5 amino acid alterations such as substitutions with respect to the stated sequence.

A variant of a polypeptide for which the sequence is known or disclosed herein may in certain embodiments be the same length or shorter than that sequence. In other embodiments the polypeptide (e.g. a DNA-PK$_{cs}$-like polypeptide or an EGGDVDDLLDMI polypeptide or a polypeptide consisting of any of the amino acid sequences of any of the Homology Regions shown in FIG. 1) may be included in a larger polypeptide. For example, 1, 2, 3, 4 or 5, 10, 20 or more additional amino acid residues, adjacent to a native form of the specific polypeptide or heterologous thereto may be included at one end or both ends of the polypeptide.

Variants include mutants, alleles, derivatives and fragments of the stated sequence. Derivatives of polypeptides include the polypeptide linked to a coupling partner, e.g. an effector molecule, a label, a drug, a toxin and/or,a carrier or transport molecule, a nd/or a targeting molecule such as an antibody or binding fragment thereof or other ligand. Techniques for coupling to both peptidyl and non-peptidyl coupling partners are well known in the art. In one embodiment, the carrier molecule is a 16 amino acid peptide sequence derived from the homeodomain of Antennapedia (e.g. as sold under the name "Penetratin"), which can be coupled to a peptide via a terminal Cys residue. The "Penetratin" molecule and its properties are described in WO 91/18981.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Homology may be taken over the full-length of a sequence or over a part, such as 20, 30, 40, 50, 60, 70, 80, 90, 100, 120, 150, 200 contiguous nucleotides or amino acids. That two nucleotide sequences are said to share "homology" or be "homologous" is based on sequence comparison. Any phylogenetic relationship is irrelevant for this. Those skilled in the art routinely refer to homology between nucleotide sequences with no implication for evolutionary origin. Two homologous nucleotide sequences may also be said to be "similar" or have a certain per centage similarity or a certain per centage identity.

In general it is not critical which of the various standard algorithms are used to determine how homologous two nucleotide sequences are with one another. A preferred algorithm may be GAP, which uses the alignment method of Needleman and Wunsch (*J. Mol. Biol.* (1970) 48, 443–453) and is included in the Program Manual or the Wisconsin Package, Version 8, September 1994, Genetics Computer Group, 575 Science Drive, Madison, Wis., USA). In the absence of instructions to the contrary, the skilled person would understand to use the default parameters with the aim of maximizing alignment, with a gap creation penalty=12 and gap extension penalty=4.

Similarity or homology (the terms are used interchangeably) or identity may be as defined and determined by the TBLASTN program, of Altschul et al. (1990) *J. Mol. Biol.* 215: 403–10, or BestFit, which is part of the Wisconsin Package, Version 8, September 1994, (Genetics Computer Group, 575 Science Drive, Madison, Wis., USA, Wisconsin 53711). Preferably sequence comparisons are made using FASTA and FASTP (see Pearson & Lipman, 1988. Methods in Enzymology 183: 63–98). Parameters are preferably set, using the default matrix, as follows: Gapopen (penalty for the first residue in a gap): −12 for proteins/−16 for DNA; Gapext (penalty for additional residues in a gap): −2 for proteins/−4 for DNA; KTUP word length: 2 for proteins/6 for DNA.

Nucleic acid sequence homology may be determined by means of selective hybridisation between molecules under stringent conditions.

Preliminary experiments may be performed by hybridising under low stringency conditions. For probing, preferred conditions are those which are stringent enough for there to be a simple pattern with a small number of hybridisations identified as positive which can be investigated further.

For example, hybridizations may be performed, according to the method of Sambrook et al. (below) using a hybridization solution comprising: 5×SSC (wherein 'SSC'=0.15 M sodium chloride; 0.15 M sodium citrate; pH 7), 5×Denhardt's reagent, 0.5–1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology is (Sambrook et al., 1989): $T_m=81.5°$ C.$+16.6$Log$[Na+]+0.41$(% G+C)$-0.63$(% formamide)$-600/$#bp in duplex.

As an illustration of the above formula, using $[Na+]=[0.368]$ and 50-% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

It is well known in the art to increase stringency of hybridisation gradually until only a few positive clones remain. Other suitable conditions include, e.g. for detection of sequences that are about 80–90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

Polypeptides in accordance with and for use in the present invention, e.g. EGGDVDDLLDMI polypeptides or DNA-$PK_{cs}$-like polypeptides or peptides or polypeptides consisting of a Ku Homology Region peptide as defined, may be generated wholly or partly by chemical synthesis, in accordance with well-established techniques, such as standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry.

Another convenient way of producing peptides and polypeptides according to or for use in the present invention is to express encoding nucleic acid, by use of nucleic acid in an expression system.

Nucleic acid molecules encoding a peptide or polypeptide as defined herein in accordance with the present invention represent further aspects of the present invention in their own right.

Generally, nucleic acid according to, or for use in, the present invention is provided as an isolate, in isolated and/or purified form, or free or substantially free of material with which it is naturally associated, such as free or substantially free of nucleic acid flanking the gene in the (e.g. human) genome, except possibly one or more regulatory sequence(s) for expression. Nucleic acid may be wholly or partially synthetic and may include genomic DNA, cDNA or RNA.

Nucleic acid sequences encoding a peptide or polypeptide according to the invention, may be readily prepared by the skilled person using the information and references contained herein and techniques known in the art (for example, see Sambrook, Fritsch and Maniatis, "Molecular Cloning, A Laboratory Manual, Cold Spring Harbor Laboratory Press, 1989, and Ausubel et al, Short Protocols in Molecular Biology, John Wiley and Sons, 1992). These techniques include (i) the use of the polymerase chain reaction (PCR) to amplify samples of such nucleic acid, e.g. from genomic sources, (ii) chemical synthesis, or (iii) preparing cDNA sequences.

DNA encoding a peptide or polypeptide according to the invention may be generated and used in any suitable way known to those of skill in the art, including taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is. to amplify the relevant portion of the DNA with suitable PCR primers.

Modifications to a nucleic acid sequence may be made, e.g. using site directed mutagenesis, to lead to the production of modified forms of a polypeptide, e.g. an EGGDVDDLL-DMI polypeptide, e.g. a mutant form of such a sequence, or to take account of codon preference in the host cells used to express the nucleic acid.

In order to obtain expression of the nucleic acid sequences of the invention, the sequences may be incorporated in a vector having one or more control sequences operably linked to the nucleic acid to control its expression. Vectors may contain appropriate regulatory sequences, including promoter sequences, terminator fragments, polyadenylation sequences, enhancer sequences, marker genes and other sequences as appropriate, e.g. nucleic acid sequences so that the polypeptide or peptide is produced as a fusion and/or nucleic acid encoding secretion signals so that the polypeptide produced in the host cell is secreted from the cell. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

A peptide or polypeptide according to the invention may then be obtained by transforming the vectors into host cells in which the vector is functional, culturing the host cells so that the encoded peptide or polypeptide, e.g. EGGDVD-DLLDMI polypeptide, is produced and recovering the sequence from the host cells or the surrounding medium.

A further aspect of the present invention provides a host cell containing heterologous nucleic acid as disclosed herein.

Systems for cloning and expression of polypeptides in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*.

The nucleic acid of the invention may be integrated into the genome (e.g. chromosome) of the host cell. Integration may be promoted by inclusion of sequences which promote recombination with the genome, in accordance with standard techniques. The nucleic acid may be on an extrachromosomal vector within the cell, or otherwise identifiably heterologous or foreign to the cell.

Thus, a host cell containing nucleic acid according to the present invention, e.g. as a result of introduction of the nucleic acid into the cell or into an ancestor of the cell (which introduction may take place in vivo or ex vivo), may be comprised (e.g. in the soma) within an organism which is an animal, particularly a mammal, which may be human or non-human, such as rabbit, guinea pig, rat, mouse or other rodent, cat, dog, pig, sheep, goat, cattle or horse, or a bird, such as a chicken.

Genetically modified or transgenic animals or birds comprising such a cell are also provided as further aspects of the present invention.

This may have a therapeutic aim. (Gene therapy is discussed elsewhere herein). Also, the presence of a mutant, allele, derivative or other variant sequence within cells of an organism may allow the organism to be used as a model in studying substances which modulate binding of a peptide to a binding partner, e.g. an EGGDVDDLLDMI polypeptide to a DNA-$PK_{CS}$-like polypeptide. Conveniently, however, at least preliminary assays for such substances may be carried out in vitro, that is within host cells or in cell-free systems. Where an effect of a test compound is established on cells in vitro, those cells or cells of the same or similar type may be grafted into an appropriate host animal for in vivo testing.

A further aspect provides a method which includes introducing a nucleic acid molecule of the invention into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

Marker genes such as antibiotic resistance or sensitivity genes may be used in identifying clones containing nucleic acid of interest, as is well known in the art. The introduction may be followed by causing or allowing expression from the nucleic acid, e.g. by culturing host cells (which may include cells actually transformed although. more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

Introduction into target cells of nucleic acid of the present invention may take place in vivo by way of gene therapy, for instance to modulate e.g. disrupt or interfere with, binding of an EGGDVDDLLDMI polypeptide to a DNA-$PK_{cs}$-like polypeptide. In light of the above, the present invention also provides a method of making a peptide or polypeptide as defined, the method including expression from nucleic acid encoding the peptide or polypepitde. This may conveniently be achieved by growing a host cell containing the nucleic acid in culture under appropriate conditions which cause or allow expression of the peptide or polypeptide. Note however that expression may also be carried out in in vitro systems, e.g. reticulocyte lysate, as discussed elsewhere herein.

As discussed above, the present invention provides EGGDVDDLLDMI polypeptides, methods of identifying further EGGDVDDLLDMI polypeptides which have the ability to bind to a DNA-$PK_{cs}$-like polypeptide and methods of identifying DNA-$PK_{CS}$-like polypeptides which have the ability to bind to an EGGDVDDLLDMI polypeptide.

EGGDVDDLLDMI polypeptides having the ability to bind to a DNA-$PK_{cs}$-like polypeptide will have the ability to modulate, e.g. interfere with, binding of that DNA-$PK_{cs}$-like poylpeptide to proteins harbouring that EGGDVDDLLDMI polypeptide or variants thereof, e.g. to proteins which are in vivo binding partners of that DNA-$PK_{cs}$-like polypeptide.

Accordingly, in still further aspects, the present invention provides for assays and methods of screening for a substance which modulates, e.g. inhibits, reduces or interferes with, binding of a DNA-$PK_{cs}$-like polypeptide to an EGGDVDDLLDMI polypeptide, and for the use of DNA-$PK_{cs}$-like polypeptides and/or EGGDVDDLLDMI polypeptides in these screening methods and assays.

Such a method may include:

(i) bringing a DNA-$PK_{cs}$-like polypeptide into contact with an EGGDVDDLLDMI polypeptide in the presence of one or more test substances;

(ii) determining binding of the DNA-$PK_{cs}$-like polypeptide to the EGGDVDDLLDMI polypeptide.

Binding in the presence of a test substance may be compared with binding of the DNA-$PK_{cs}$-like polypeptide to the EGGDVDDLLDMI polypeptide in comparable reaction medium and conditions in the absence of a test substance. A test substance able to modulate the binding may be identified.

Agents which modulate e.g. increase or potentiate interaction between a DNA-$PK_{cs}$-like polypeptide and an EGGDVDDLLDMI polypeptide may be identified using conditions which, in the absence of a positively-testing agent, prevent or impair the substances interacting.

A difference in the binding of the DNA-$PK_{cs}$-like polypeptide to the EGGDVDDLLDMI polypeptide between the treated and untreated conditions is indicative of a modulating effect of the relevant test substance(s).

Further aspects of the invention provide assay methods for identifying or obtaining agents which modulate, especially interfere with, interaction between Ku70 or Ku80 and a binding partner, via a Homology Region as identified herein.

Such methods may comprise (i) bringing a Ku Homology Region Peptide into contact with a binding partner in the presence of one or more test substances;

(ii) determining binding of the Ku Homology Region Peptide to the binding partner.

Binding may be determined by any suitable method known to those skilled in the art. Examples of such methods are described below.

In any assay method according to the invention, the amount of test substance or compound which may be added to an assay of the invention will normally be determined by trial and error depending upon the type of compound used. Typically, from about 0.001 nM to 1 mM or more concentrations of putative inhibitor compound may be used, for example from 0.01 nM to 100 $\mu$M, e.g. 0.1 to 50 $\mu$M, such as about 10 $\mu$M. Greater concentrations may be used when a peptide is the test substance. Even a molecule which has a weak effect may be a useful lead compound for further investigation and development.

Compounds which may be screened may be natural or synthetic chemical compounds used in drug screening programmes. Extracts of plants, microbes or other organisms, which contain several characterised or uncharacterised components may also be used.

It is worth noting that combinatorial library technology provides an efficient way of testing a potentially vast number of different substances for ability to modulate an interaction. Such libraries and their use are known in the art, for all manner of natural products, small molecules and peptides, among others. The use of peptide libraries may be preferred in certain circumstances.

In various aspects the present invention provides a modulator identified by a screening method of the invention, e.g. a substance which interferes with or interrupts, increases or potentiates binding of a DNA-PK$_{cs}$-like polypeptide (e.g. DNA-PK$_{cs}$) to a target EGGDVDDLLDMI polypeptide (e.g. Ku80 or an EGGDVDDLLDMI polypeptide of the present invention), or Ku70 and/or Ku80 to each other or a binding partner (via a Homology Region).

Following identification of a modulator, the substance may be purified and/or investigated further and/or manufactured. A modulator may be used to obtain peptidyl or non-peptidyl mimetics, e.g. by methods well known to those skilled in the art and discussed herein. It may be used in a therapeutic context as discussed below.

One class of modulators comprises peptides comprising the amino acid sequence EGGDVDDLLDMI (SEQ ID NO:1) or variants thereof, which peptides have the ability to bind to a DNA-PK$_{CS}$-like polypeptide. A further class of modulators comprises peptide fragments of DNA-PK$_{CS}$-like polypeptides, or variants thereof, particularly fragments of DNA-PK$_{CS}$-like polypeptides which contain sequence motifs that have been identified (e.g. in a screening method of the present invention) as being involved in binding of the DNA-PK$_{CS}$-like polypeptide to an EGGDVDDLLDMI sequence (SEQ ID NO:1).

Suitable peptide modulators are those which bind to Ku80 or to an EGGDVDDLLDMI polypeptide shown in FIG. 4 and/or which have a length of 50–55, 55–60, 60–65, 65–70, 70–75, 75–80, 80–85, 85–90, 90–95, 95–100, or more than 100 amino acids. Nucleic acid encoding such peptide frgaments, vectors and host cells containing such nucleic acid, and methods of expressing nucleic acid encoding such fragments are further aspects of the present invention. The discussion included herein relating to the construction, use and expression of peptides and polypeptides and encoding nucleic acid applies to such embodiments as appropriate.

Antibodies directed to the a peptide disclosed herein, a Ku Homology Region peptide or EGGDVDDLLDMI, or to a sequence in a DNA-PK$_{cs}$-like polypeptide identified (e.g. in a method of the present invention) as being involved in an interaction with an EGGDVDDLLDMI polypeptide, form further classes of putative inhibitor compounds and represent individual aspects of the invention in their own right. Candidate inhibitor antibodies may be characterised and their binding regions determined to provide single chain antibodies and fragments thereof which are responsible for disrupting the binding.

Antibodies in accordance with and/or for use in the present invention may be obtained using techniques which are standard in the art. Methods of producing antibodies include immunising a mammal (e.g. mouse, rat, rabbit, horse, goat, sheep or monkey) with a polypeptide or fragment thereof, e.g. with a EGGDVDDLLDMI polypeptide (e.g. with the polypeptide EGGDVDDLLDMI (SEQ ID NO:1) or a variant thereof), or with a DNA-PK$_{CS}$-like polypeptide, or with a Ku Homology Region Peptide. Antibodies may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80–82). Isolation of antibodies and/or antibody-producing cells from an animal may be accompanied by a step of sacrificing the animal.

As an alternative or supplement to immunising a mammal with a peptide, an antibody specific for a peptide or polypeptide of interest may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with the relevant peptide or polypeptide (or fragments thereof), or may be one constructed using sequences obtained from an organism which has been exposed to the antigen of interest.

Antibodies according to and/or for use in the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimicks that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP184187A, GB 2188638A or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule. The mode of determining binding is not a feature of the present invention and those skilled in the art are able to choose a suitable mode according to their preference and general knowledge.

Antibodies may also be used in purifying and/or isolating a polypeptide, e.g. an EGGDVDDLLDMI polypeptide or a Ku polypeptide or DNA-PK$_{CS}$-like polypeptide for instance following production of the polypeptide by expression from encoding nucleic acid therefor. The antibodies may be respectively directed to the amino acid sequence EGGD-VDDLLDMI (SEQ ID NO:1), to a Ku Homology Region Peptide, or to a region of a DNA-PK$_{CS}$-like polypeptide identified (e.g. by a method of the present invention) as having the ability to interact with an EGGDVDDLLDMI polypeptide. Antibodies may be useful in a therapeutic context (which may include prophylaxis) e.g. to disrupt binding of a DNA-PK$_{CS}$-like polypeptide to an EGGDVD-DLLDMI polypeptide with a view to inhibiting the activity of either component. Antibodies can for instance be microinjected into cells, e.g. at a tumour site, subject to radio- and/or chemo-therapy (as discussed already above). Antibodies may be employed in accordance with the present invention for other therapeutic and non-therapeutic purposes which are discussed elsewhere herein.

In a further aspect, the present invention provides the use of a peptide as disclosed herein in a method of designing a peptide or non-peptidyl mimetic of the polypeptide. A mimetic may be able to bind to a DNA-PK$_{CS}$-like polypeptide and/or modulate interaction between a DNA-PK$_{CS}$-like polypeptide and an EGGDVDDLLDMI polypeptide. A EGGDVDDLLDMI polypeptide used in such a method may be the amino acid sequence EGGDVDDLLDMI (SEQ ID NO:1) or a variant thereof, or an EGGDVDDLLDMI polypeptide of the present invention, e.g. one shown in FIG. 4.

The present invention similarly provides for the use of a DNA-PK$_{CS}$-like polypeptide, for example DNA-PK$_{CS}$, particularly a DNA-PK$_{CS}$-like polypeptide identified as having the ability to bind to the amino acid sequence EGGDVD-DLLDMI (SEQ ID NO:1), in a method of designing a peptide or non-peptidyl mimetic of a DNA-PK$_{CS}$-like polypeptide, which mimetic is able to bind to a given EGGDVDDLLDMI polypeptide, e.g. to Ku80.

Accordingly, the present invention provides a method of designing a mimetic of a EGGDVDDLLDMI polypeptide which has the biological activity of binding to a DNA-PK$_{cs}$-like polypeptide (e.g. DNA-PK$_{cs}$), or a method of designing a mimetic of a DNA-PK$_{cs}$-like polypeptide which has biological activity of binding to a target EGGDVDDLLDMI polypeptide (e.g. to Ku80 and/or to to an EGGDVDDLL-DMI polypeptide of the present invention), or a method of designing a mimetic of a Ku Homology Region Peptide, said method comprising:

(i) analysing a substance having the biological activity to determine the amino acid residues essential and important for the activity to define a pharmacophore; and, (ii) modelling the pharmacophore to design and/or screen candidate mimetics having the biological activity.

Suitable modelling techniques are known in the art. This includes the study of the bonding between peptides or polypeptides and to design compounds which contain functional groups arranged in such a manner that they could reproduced that bonding.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, for instance polypeptides of the invention may not be well suited as active agents for oral compositions as they tend to be quickly degraded by proteases in the alimentary canal.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of the above approach, the three-dimensional structure of a ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

The mimetic or mimetics found by any of the approaches described herein may be used in the assay methods of the present invention to determine whether they have the ability to bind to the relevant compound, e.g. to a DNA-PK$_{cs}$-like polypeptide (e.g. DNA-PK$_{CS}$) or to a target EGGDVDDLL-DMI polypeptide(e.g. to Ku80 and/or to an EGGDVDDLL-DMI polypeptide of the present invention).

Mimetics obtained by a method of the invention form a further aspect of the invention.

The invention further provides various therapeutic methods and uses of one or more substances selected from (i) an EGGDVDDLLDMI polypeptide, (e.g. an EGGDVDDLL-DMI polypeptide according to the present invention, a fragment of Ku80 comprising the sequence EGGDVDDLL-DMI (SEQ ID NO:1), an EGGDVDDLLDMI polypeptide identified in accordance with a method of the present invention); (ii) a DNA-PK$_{CS}$-like polypeptide, (e.g. a variant of DNA-PK$_{CS}$, e.g. fragment of DNA-PK$_{CS}$, a DNA-PK$_{CS}$-like polypeptide identified by a screening method of the present invention); (iii) any peptide or polypeptide disclosed herein, e.g. a Ku Homology Region Peptide; (iv) a modulator identified by a screening method of the present invention; (v) a mimetic of any of the above substances which can bind to a DNA-PK$_{CS}$-like polypeptide or EGGDVDDLL-DMI polypeptide.

The therapeutic/prophylactic purpose of such a method or use may be the modulation, e.g. disruption or interference, of the binding of a DNA-PK$_{cs}$-like polypeptide to an EGG-DVDDLLDMI polypeptide, or a Ku Homology Region to a binding partner, e.g. to modulate any activity mediated by virtue of such binding.

The therapeutic/prophylactic purpose may for example be:

(i) Chemotherapy and/or radiotherapy, e.g. sensitising tumours or other cells to radiation or chemotherapy, e.g. modulating (for example inhibiting) interactions of Ku70, Ku80 and/or DNA-PK$_{cs}$ leading to e.g. impairment of tumour proliferation and/or growth;

(ii) Modulation (e.g. inhibition) of infection of pathogens (e.g. viruses) whose infectivity is influenced by Ku and/or DNA-PK$_{CS}$, e.g. inhibition of retroviral integration;

(iii) Controlling cell e.g. tumour growth via modulation of telomere function;

(iv) Modulating V(D)J recombination or other genomic rearrangement that employs Ku and/or DNA-PK$_{cs}$.

In various further aspects the present invention thus provides a pharmaceutical composition, medicament, drug or other composition for such a purpose, the composition comprising one or more of the substances set out above, the use of such a substance in a method of medical treatment, a method comprising administration of such a substance or composition to a patient, e.g. for treatment (which may include preventative treatment) of a medical condition, e.g. a condition associated with a defect or disorder in DNA repair, or cell cycle control, e.g. for treatment of a disorder of cellular proliferation such as cancer, use of such a substance in the manufacture of a composition, medicament or drug for administration for such a purpose, e.g. for treatment of a proliferative disorder, and a method of making a pharmaceutical composition comprising admixing such a substance with a pharmaceutically acceptable excipient, vehicle or carrier, and optionally other ingredients.

The substances may be used as sole active agents or in combination with one another or with any other active substance, e.g. for anti-tumour therapy another anti-tumour compound or therapy, such as radiotherapy or chemotherapy. Whatever the substance used in a method of medical treatment of the present invention, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practioners and other medical doctors.

A substance or composition may be administered alone or in combination with other treatments, either simultaneously or sequentially dependent upon the condition to be treated, e.g. cancer.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations.

Examples of techniques and protocols mentioned above can be found in Remington's Pharmaceutical Sciences, 16th edition, Osol, A. (ed), 1980.

The substance or composition may be administered in a localised manner to a tumour site or other desired site or may be delivered in a manner in which it targets tumour or other cells.

Targeting therapies may be used to deliver the active substance more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Instead of administering such substances directly, they may be produced in the target cells by expression from an encoding nucleic acid introduced into the cells, e.g. from a viral vector. The vector may be targeted to the specific cells to be treated, or it may contain regulatory elements which are switched on more or less selectively by the target cells.

Nucleic acid encoding the substance e.g. a polypeptide able to modulate, e.g. interfere with, the binding of a DNA-PK$_{cs}$-like polypeptide to an EGGDVDDLLDMI polypeptide may thus be used in methods of gene therapy, for instance in treatment of individuals, e.g. with the aim of preventing or curing (wholly or partially) a disorder.

Vectors such as viral vectors have been used in the prior art to introduce nucleic acid into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors in gene therapy other known methods of introducing nucleic acid into cells includes mechanical techniques such as microinjection, transfer mediated by liposomes and receptor-mediated DNA transfer.

Receptor-mediated gene transfer, in which the nucleic acid is linked to a protein ligand via polylysine, with the ligand being specific for a receptor present on the surface of the target cells, is an example of a technique for specifically targeting nucleic acid to particular cells.

A peptide, polypeptide or other substance according to the present invention, e.g. a nucleic acid molecule which encodes a peptide or polypeptide, may be provided in a kit, e.g. sealed in a suitable container which protects its contents from the external environment. Such a kit may include instructions for use.

In still further aspects the present invention provides for the purification of a DNA-PK$_{cs}$-like polypeptide or protein containing a DNA-PK$_{cs}$-like polypeptide, or for the purification of an EGGDVDDLLDMI polypeptide. The invention also provides for a purified DNA-PK$_{cs}$-like polypeptide or protein containing a DNA-PK$_{cs}$-like polypeptide and a purified EGGDVDDLLDMI polypeptide. The purified protein or polypeptide may be about,10% pure, more preferably about 20% pure, more preferably about 30% pure, more preferably about 40% pure, more preferably about 50% pure, more preferably about 60% pure, more preferably about 70% pure, more preferably about 80% pure, more preferably about 90% pure, more preferably about 95% pure, or substantially pure.

The present invention thus provides a method of purifying a DNA-PK$_{CS}$-like polypeptide or protein containing a DNA-PK$_{CS}$-like polypeptide, the method including contacting the DNA-PK$_{CS}$-like polypeptide with an EGGDVDDLLDMI peptide. The present inventors have already shown that the DNA-PK$_{CS}$-like polypeptide human DNA-PK$_{CS}$ can be purified to virtual homogeneity in a single step using a peptide of amino acid sequence EGGDVDDLLDMI (SEQ ID NO:1).

A mixture of material including a DNA-PK$_{cs}$-like polypeptide or protein containing a DNA-PK$_{cs}$-like polypeptide may be contacted against immobilised EGGD-VDDLLDMI polypeptide (e.g. immobilised either covalently or non-covalently such as via a specific binding molecule such as streptavidin or biotin) and molecules which do not bind to the phosphopeptide are washed off.

Likewise, the invention provides a method of purifying an EGGDVDDLLDMI polypeptide, the method including contacting material containing the polypeptide with a DNA-PK$_{cs}$-like polypeptide.

Preferred EGGDVDDLLDMI polypeptides and DNA-PK$_{cs}$-like polypeptides for use in methods of the invention are discussed elsewhere herein.

The DNA-PK$_{cs}$-like polypeptide or protein containing a DNA-PK$_{cs}$-like polypeptide which is contacted with the EGGDVDDLLDMI polypeptide, or the EGGDVDDLL-DMI polypeptide which is contacted with the DNA-PK$_{cs}$-like polypeptide, in a purification method of the present invention, may be in a mixture of molecules, such as a cellular extract, such as a normal cell of an organism such as a human or a recombinant host cell expressing the protein or polypeptide from encoding DNA, such as a bacterial, eukaryotic (e.g. mammalian or yeast) or insect cell, such as in a baculovirus expression system. Purification may follow production of such a polypeptide recombinantly in a suitable expression system, such as a cell, by expression from encoding nucleic acid. Following purification, the DNA-PK$_{cs}$-like polypeptide or protein containing the DNA-PK$_{cs}$-like polypeptide or the EGGDVDDLLDMI polypeptide may be used as desired, e.g. in an assay for an agent which modulates its activity, e.g. binding, in raising or obtaining a specific antibody or other binding molecule, or in a therapeutic context.

Methods of determining the binding of a DNA-PK$_{CS}$-like polypeptide to an EGGDVDDLLDMI polypeptide, of identifying a. DNA-PK$_{cs}$-like polypeptide, of screening for an EGGDVDDLLDMI polypeptide able to bind to a DNA-PK$_{cs}$-like polypeptide, and of screening for an agent able to modulate binding of a DNA-PK$_{cs}$-like polypeptide to an EGGDVDDLLDMI polypeptide, include methods in which a suitable end-point is used to assess binding.

Binding may be determined by any number of techniques known in the art, qualitative or quantitative. They include techniques such as radioimmunosassay, co-immunoprecipitation, scintillation proximetry assay and ELISA methods.

Binding of a DNA-PK$_{CS}$-like polypeptide (e.g. DNA-PK$_{CS}$) to a target EGGDVDDLLDMI polypeptide (e.g. to a peptide of amino acid sequence EGGDVDDLLDMI (SEQ ID NO:1)) may be studied by labelling either one with a detectable label and bringing it into contact with the other which may have been immobilised on a solid support.

Suitable detectable labels, especially for peptidyl substances include $^{35}$S-methionine which may be incorporated into recombinantly produced peptides and polypeptides. Recombinantly produced peptides and polypeptides may also be expressed as a fusion protein containing an epitope which can be labelled with an antibody.

The polypeptide which is immobilized on a solid support may be immobilized using an antibody against that polypeptide bound to a solid support or via other technologies which are known per se. A preferred in vitro interaction may utilise a fusion polypeptide including glutathione-S-transferase (GST). This may be immobilized on glutathione agarose beads. In an in vitro assay format of the type described above a test modulator can be assayed by determining its ability to diminish the amount of labelled polypeptide (e.g. labelled EGGDVDDLLDMI polypeptide) which binds to the immobilized GST-fusion polypeptide (e.g. immobilised fusion polypeptide of GST and a DNA-PK$_{cs}$-like polypeptide). This may be determined by fractionating the glutathione-agarose beads by SDS-polyacrylamide gel electrophoresis. Alternatively, the beads may be rinsed to remove unbound polypeptide and the amount of polypeptide which has bound can be determined by counting the amount of label present in, for example, a suitable scintillation counter.

Binding or interaction of a DNA-PK$_{cs}$-like polypeptide and an EGGDVDDLLDMI polypeptide may also be determined using a two-hybrid assay.

For example, a DNA-PK$_{cs}$-like polypeptide polypeptide or an EGGDVDDLLDMI polypeptide may be fused to a DNA binding domain such as that of the yeast transcription factor GAL4. The GAL4 transcription factor includes two functional domains. These domains are the DNA binding domain (GAL4DBD) and the GAL4 transcriptional activation domain (GAL4TAD). By fusing the DNA-PK$_{cs}$-like polypeptide to one of those domains, and an EGGDVD-DLLDMI polypeptide to the respective counterpart, a functional GAL4 transcription factor is restored only when the DNA-PK$_{cs}$-like polypeptide and EGGDVDDLLDMI polypeptide interact. Thus, interaction of these polypeptides may be measured by the use of a reporter gene linked to a GAL4 DNA binding site which is capable of activating transcription of said reporter gene.

This two hybrid assay format is described by Fields and Song, 1989, Nature 340; 245–246. It can be used in both mammalian cells and in yeast. Other combinations of DNA binding domain and transcriptional activation domain are available in the art and may be preferred, such as the LexA DNA binding domain and the VP60 transcriptional activation domain.

When looking for substances which interfere with binding of (for example) a DNA-PK$_{cs}$-like polypeptide to an EGG-DVDDLLDMI polypeptide, a DNA-PK$_{cs}$-like polypeptide or a EGGDVDDLLDMI polypeptide may be employed as a fusion with (e.g.) the LexA DNA binding domain, and the counterpart polypeptide containing the DNA-PK$_{cs}$-like polypeptide or EGGDVDDLLDMI polypeptide as a fusion with (e.g.) VP60. An expression cassette may be used to express a test peptide within a host cell. The expression cassette may be one vector from a library of expression vectors which encode a diverse range of peptides. A reduction in reporter gene expression (e.g. in the case of β-galactosidase a weakening of the blue colour) results from the expression of a peptide which disrupts the DNA-PK$_{cs}$-like polypeptide/EGGDVDDLLDMI polypeptide interaction, which interaction is required for transcriptional activation of the β-galactosidase gene. Where a test substance is not peptidyl and may not be expressed from encoding nucleic acid within a said third expression cassette, a similar system may be employed with the test substance supplied exogenously.

An assay or screening method according to the present invention may thus take the form of an in vivo assay. The end-point of an in vivo assay, that is to say the property which is determined in order to assess the binding of a DNA-PK$_{cs}$-like polypeptide to an EGGDVDDLLDMI polypeptide (e.g. to assess whether a test agent has an effect on the binding of a DNA-PK$_{cs}$-like polypeptide to a EGG-DVDDLLDMI polypeptide) may be a biological activity of the DNA-PK$_{cs}$-like polypeptide or a biological activity of the EGGDVDDLLDMI polypeptide, whichever is appropriate. As noted, those skilled in the art well appreciate the need for and design of appropriate controls for validation of results.

As end points for in vivo assays employing human DNA-PK$_{cs}$ or a homologue/orthologue thereof, and/or Ku, the effect on DNA repair, cell viability, cell killing, radiosensitivity, V(D)J recomination, cell cycle arrest. In yeast, P element transposition, and mating type switching may be measured. Suitable methods are known to those skilled in the art.

Various further aspects and embodiments of the present invention will be apparent to those skilled in the art in view of the present disclosure. Certain aspects and embodiments of the invention will now be illustrated by way of example and with reference to the figures described below.

BRIEF DESCRIPTION OF THE FIGURES

FIG. 1 shows a sequence alignment of Ku70 and Ku80 sequences (SEQ ID NOS:2–9). At each position in the alignment, amino acid residues with conserved identity in three or more Ku subunit proteins are shaded black, those with similarly conserved chemical or physical properties are shaded grey. The positions of the most highly conserved regions termed Homology Regions 1–6 (HRs 1–6) are marked by shaded boxes above the aligned sequences. The HRs and specific C-terminal extension of Ku80 have been rendered in the same shading as used in the representations of Ku80 and Ku70 deletion mutants shown in FIGS. 2 and 3. The members of the alignment are as follows: *Homo sapiens* Ku70 (HsKu70) (SEQ ID NO:2), *Gallus gallus* Ku70 (GgKu70) (SEQ ID NO:3), *Rhipicephalus appendiculatus* Ku70 (RaKu70) (SEQ ID NO:4), *Drosophila Melanogaster* Ku70 (DmKu70) (SEQ ID NO:5), *Saccharomyces cerevisiae* Ku70 (ScKu70) (SEQ ID NO:6), *Homo sapiens* Ku80 (HsKu80) (SEQ ID NO:7), *Caenorhabditis elegans* Ku80 (CeKu80) (SEQ ID NO:8) and *Saccharomyces cerevisiae* Ku80 (ScKu80) (SEQ ID NO:9).

FIG. 4 is a schematic diagram of the Ku80 deletions used to define the region of Ku80 that interacts with DNA-PK$_{cs}$. Full length Ku80 is shown at the top with deletion mutants drawn to scale below.

FIG. 5 is a schematic diagram of the C-terminus of human Ku80, amino acids 609–733 (SEQ ID NO:11), and the sequence of 5 peptides derived therefrom (SEQ ID NOS:12–15 and SEQ ID NO:1). These peptides, designated A–E were generated with an N-terminal biotin group followed by the sequence Ser-Gly-Ser-Gly (SEQ ID NO:10) as a linker to the Ku80 derived sequence shown.

FIG. 6 is a multiple sequence alignment of the C-terminal regions of Ku80 homologues showing high sequence conservation between mammalian (*C. griseus*, SEQ ID NO:17, *M. musculus*, SEQ ID NO:18, and *H. sapiens*, SEQ ID NO:16) Ku80 homologues in the final 13 amino acid residues. The location of the DNA-PKcs interaction motif defined within human Ku80 (the final 12 amino acid residues) is indicated.

MATERIALS AND METHODS

Yeast 2-hybrid Assay

Figure 2:
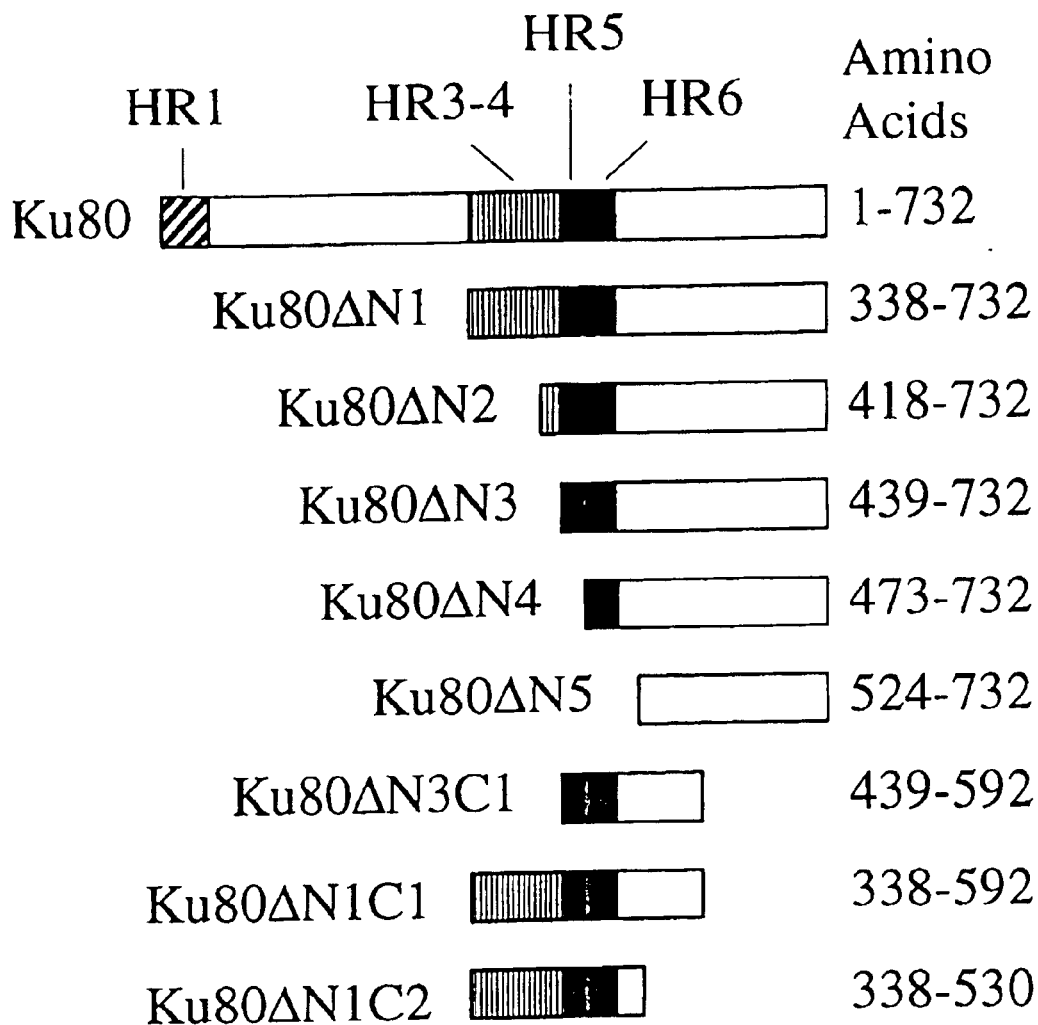
FIG. 2 shows the Ku80 deletion derivatives used to investigate the regions of Ku80 able to interact with full length Ku70. The deletion derivatives were expressed as GST fusion proteins. Full length Ku80 is represented by the uppermost bar. The positions of the Homology Regions (HRs) defined in FIG. 1 are indicated. For each HR, the shading is the same as used in FIG. 1. Deletion mutants are represented by shaded bars below this, drawn to scale with the numbers of the first and last amino acid residues of each deletion printed to the right of each bar.

A large fragment of Ku70 (corresponding to residues 213–590) was PCR amplified and cloned into the yeast 2-hybrid "bait" vector pEG202 to generate a fusion with the DNA-binding domain Lex202 (Lex-Ku70Δ213–590), and transformed into a yeast strain, EGY48 containing the LEU2 gene under the control of 3 LexA operator sites integrated into the genome as well as the plasmid pSH18-34 containing the reporter gene GAL1-Lac Z downstream of 4 LexA operators. A HeLa cell expression library in the 2-hybrid vector pJG4–5 was transformed into the yeast containing Lex-Ku70Δ213–590. Some of the transformation was plated onto non-selective media to calculate the transformation efficiency at >10$^7$ total transformants. Yeast transformants were subjected to a 2-fold selection procedure by first plated onto medium lacking Leucine, the picking colonies that grew up onto fresh plates containing X-gal to screen for activation of the GAL1-LacZ reporter.

Generation of GST-fusion Proteins

Full length Ku70 and Ku80 were cloned in frame with the glutathione binding domain of human glutathione S-transferase (GST) by sub-cloning into pGEX2TKP (a derivative of pGEX2TKP by Pharmacia). Deletion mutants of Ku70 and Ku80 were cloned by Pfu polymerase amplification and cloning into pGEX2TKP. Expression from all pGEX2TKP constructs was carried out in either DH5α or DS941 strains of E. coli. Bacterial cell extracts were produced by sonication in Phosphate-buffered saline (PBS; 138 mM NaCl, 3 mM KCl, 10 mM Phosphate buffer pH 7.4) containing 1% Triton-X100 (Sigma) and protease inhibitor tablets (Boehringer). GST-fusion proteins were purified by passing bacterial lysates over Glutathione Agarose beads (Pharmacia) and washing extensively in PBS containing 1% Triton-X100 and then in PBS alone. The beads/proteins were stored at −80° C. prior to use.

Preparation of Biotinylated Bacterial Cell Extracts

Ku70 and Ku80 were cloned into pET30a (Novagen) to generate a N-terminal hexa-Histidine tag and expressed at low levels in E. coli (BL21 pLysS). The soluble protein fraction was prepared by lysing cells in buffer (50 mM phosphate pH 7.5, 150 mM NaCl, 0.1% β-mercaptoethanol, 0.1% Triton-X100, Boehringer Complete Protease Inhibitors) followed by centrifugation to remove insoluble material. The soluble fraction was biotinylated by addition of biotin (Sigma) to a final concentration of 0.05 mg biotin per 1 mg extract and incubating 1 hour on ice. Unreacted biotin groups were removed by addition of Glycine (0.1 M final).

GST "Pulldown" Assays from Biotinylated Extracts

Approximately 1 mg of biotinylated bacterial extract (containing His-Ku70 or His-Ku80) was diluted 2-fold in buffer (50 mM Tris pH 8.0, 250 mM NaCl, 0.1% β-mercaptoethanol, 0.1% Triton X-100, Boehringer Complete Protease Inhibitors) and incubated for 3 hours at 4° C. with 1–2 ug of GST-Ku80, GST-Ku70, or deletion derivative thereof, immobilised on beads. The beads were washed seven times in NETN buffer (180 mM NaCl, 25 mM EDTA, 20 mM Tris pH 8.0, 0.5% NP-40), boiled in SDS gel-loading buffer and half the sample subjected to polyacrylamide gel electrophoresis. Proteins were subsequently transferred to nitrocellulose membrane. Membranes were probed with streptavidin conjugated to horseradish peroxidase (GiboBRL), and visualised by ECL (Pierce) and exposure to film.

GST "Pulldown" Assays from HeLa Cell Nuclear Extract

GST-Ku70 or GST-Ku80 (0.5–2.0 μg), or deletion derivative thereof, bound to Glutathione agarose beads, was incubated with ~100 μg (10 μl) of HeLa Cell nuclear extract (NE) and 80 μl of Z' buffer (25 mM HEPES pH 6.7, 12.5 mM $MgCl_2$, 1 mM dithiothreitol, 0.1% Nonidet P40 (BDH), 20% Glycerol) containing the specified concentration of KCl (for example, 50 mM Z' contains 50 mM KCl in addition to the other buffer components). Binding reactions were incubated at 4° C. for 3–4 hours and the beads recovered by centrifugation and washed 7 times in 1 ml of Buffer X (25 mM HEPES pH 6.7, 2 mM $MgCl_2$, 1 mM Dithiothreitol, 0.4% Nonidet P40) containing the specified concentration of KCl (for example, 120 mM Buffer X contains 120 mM KCl in addition to the other buffer components). Proteins retained on the beads after washing were eluted in SDS gel-loading buffer and half of the sample subjected to polyacrylamide gel eletrophoresis and silver staining. "Pulldown" assays from purified DNA-PKcs were done as above with 400 ng of purified DNA-PKcs substituted for HeLa NE.

Peptide Interaction Assay

5 Peptides with the sequence Ser-Gly-Ser-Gly (SEQ ID NO:10) as a linker to 12 amino acid residues (SEQ ID NOS:1 and 12–15) derived from the sequence of Ku80 (see FIG. 5) were generated with a biotin moiety at the N-terminus (Khiron Technologies). Each peptide ($2 \times 10^{11}$ moles) was incubated with either 400 ng (~$10^{12}$ moles) of purified DNA-PKcs or 100 μg of crude HeLa NE in 100 μl (final) volume of Z' buffer (see above for buffer composition). Binding reactions were incubated for 2.75 hours at 4° C., then a 100 μl suspension of para-magnetic beads, containing 1:5 dilution of Dynabeads (Dynal) in Z' buffer, was added for a final 0.25 hour incubation. Dynabeads are conjugated with Streptavidin. The bead-protein complexes were be retrieved from the solution using a magnet and washed 5 times with 0.5 ml of Buffer X (see above for buffer composition). Proteins retained on the beads were eluted in SDS gel-loading buffer and subjected to polyacrylamide gel eletrophoresis and silver staining.

Purification of DNA-PKcs

The starting material for purification of DNA-PKcs was HeLa NE obtained from the Computer Cell Culture Centre, Mons, Belgium. All purification steps were performed in buffer D (20 mM HEPES pH 7.6, 2 mm $MgCl_2$, 0.2 mM EDTA, 10% Glycerol) with a specified concentration of KCl (for example 50 mM Buffer D contains 50 mM KCl in addition to the other buffer components). In a representative purification, 35 ml of HeLa NE was cleared by centrifugation and diluted to a final concentration of 50 mM Buffer D, and protease inhibitors added (Boehringer). This was loaded onto a 60 ml column of Q Sepharose (Pharmacia) and eluted in a linear salt gradient of 50–500 mM Buffer D. Under these conditions the majority of DNA-PKcs and Ku were separated into two fractions peaking at approximately 200 mM Buffer D, and 450 mM Buffer D respectively. The DNA-PKcs fraction was adjusted to 100 mM KCl using 0 mM Buffer D (salt concentration was measured by conductivity) and applied to a 10 ml column of heparin agarose (Sigma). The column was developed with a linear gradient of 100–200 mM Buffer D. The peak DNA-PKcs fraction from the heparin column was adjusted to 0.5 M ammonium sulphate and applied to a 2.5 ml column of phenyl Sepharose (Pharmacia) equilibrated in, typically, 300 mM Buffer D containing 0.5 M ammonium sulphate. Under these conditions, 100% of DNA-PKcs is retained by the column, whilst the majority of contaminating Ku flows through (as judged by western blotting using antibodies specific to the Ku subunits). The column was then washed extensively in 0 mM Buffer D containing 0.5 M ammonium sulphate, and subsequently in 0 mM Buffer D containing 0.4 M ammonium sulphate, which removes most of the remaining Ku, before applying a linear gradient of 0.4–0 M ammonium sulphate in 0 mM Buffer D. Peak DNA-PKcs fractions were dialysed into 50 mM Buffer D, applied to a 1 ml Mono-S FPLC column (Pharmacia), and eluted in a linear gradient of 50–500 mM Buffer D. Peak fractions were dialysed into 50 mM Buffer D and stored at −80° C. prior to use. The resulting protein preparation contained a single abundant polypeptide corresponding to DNA-PKcs as judged by Coomassie staining, silver staining and western blotting, with a ladder of smaller DNA-PKcs breakdown products. Western blotting of a variety of HeLa cell extracts using antibodies specific to DNA-PKcs reveals an essentially identical pattern of laddering, hence we believe that the majority of these breakdown products are present at the start of the DNA-PKcs preparation. To assess the levels of Ku contamination in the DNA-PKcs preparation we carried out quantitative western blotting using Ku-specific antibodies. In these western blots, an essentially homogeneous preparation of Ku was titrated against known amounts of our DNA-PKcs preparations. The resulting signal suggested a typical contamination level of 1 molecule of Ku to 840 molecules of DNA-PKcs.

RESULTS

A C-terminal Region of Ku80 Interacts with Ku70 in the Yeast 2-hybrid Assay

The inventors used a yeast 2-hybrid assay to screen a human HeLa cell cDNA library for proteins that interact with human Ku70 (SEQ ID NO:2). A large fragment of Ku70 (spanning residues 434 to 733), containing two putative leucine zipper motifs, was used as the "bait". A two-fold selection procedure was used (see Materials and Methods). From the first selection 530 positive colonies were picked and plated onto X-gal plates to assay for β-galactosidase activity. 55 positive clones were identified and the library plasmids contained within these clones were rescued into E. coli. Notably, bacterial colony hybridisation to a radiolabelled Ku80 DNA probe revealed that 44% gave a strong positive signal, and when these clones were sequenced, all were found to contain the Ku80 cDNA. The retrieved plasmids comprised eight distinct Ku80 cDNA clones: all contained the poly(A) tail of the Ku80 cDNA but differed in their 5' ends. The different 5' termini were highly clustered, all falling to within 27 nucleotides of each other. The smallest clone encodes the C-terminal 293 amino acid residues of Ku80, defining this region as sufficient for interaction with Ku70 in this assay.

Analysis of Interactions Between Bacterially-expressed Ku70 and Ku80 Deletion Derivatives In a complementary approach to the yeast 2-hybrid technique, the inventors used a "pull-down" assay to detect interactions between recombinant deletion derivatives of the two Ku subunits. To first establish the utility of this approach, they assayed for interaction between full-length Ku70 and Ku80 in this system. Both Ku subunits were sub-cloned into bacterial expression vectors designed to express them either as a GST-fusion or with an N-terminal hexa-histidine tag (see Materials and Methods). GST-Ku70 and GST-Ku80 were expressed in E. coli and purified on glutathione-agarose beads. His-Tagged Ku subunits were also expressed, and the crude unfractionated bacterial cell lysates containing either His-tagged Ku70 or His-tagged Ku80 were biotinylated at low levels (see Materials and Methods). Interaction assays were then conducted by incubating either GST-Ku80 beads with bacterial lysate containing His-Ku70, or GST-Ku70 beads with His-Ku80 lysate. The beads were next washed extensively, and then any proteins that remained bound to them were eluted in SDS-PAGE buffer, resolved on a polyacrylamide gel and western blotted. Interacting proteins were detected by probing these western blots with streptavidin that was conjugated to horse radish peroxidase (HRP). Control binding reactions were carried out using GST-alone bound beads (at a five fold molar excess over GST-Ku70/Ku80) and bacterial lysates containing either His-tagged Ku80 or His-tagged Ku70.

Of the large number of biotinylated proteins present in crude extracts, only a single species is retained efficiently on the beads in pull-downs with either GST-Ku70 or GST-Ku80. The identity of the interacting proteins as Ku80 and Ku70, respectively, was confirmed by quantitative western blotting with anti-Ku subunit antisera. In the control binding reactions using GST alone, neither Ku subunit was retained from the bacterial lysate. Although the above results suggest that the assay is detecting tight and highly specific protein-protein interactions between the two Ku subunits, another possible explanation was that the interaction might be being mediated via DNA that could have been present in the protein preparations. To address this issue, the inventors performed the above binding assays in the presence of high amounts of ethidium bromide (EtBr), which disrupts complexes between DNA and DNA-binding proteins (Lai and Herr, 1992). Importantly, the presence of EtBr has no effect on the Ku subunit interactions in the assay, demonstrating that the interaction being measured is direct.

Figure 1:
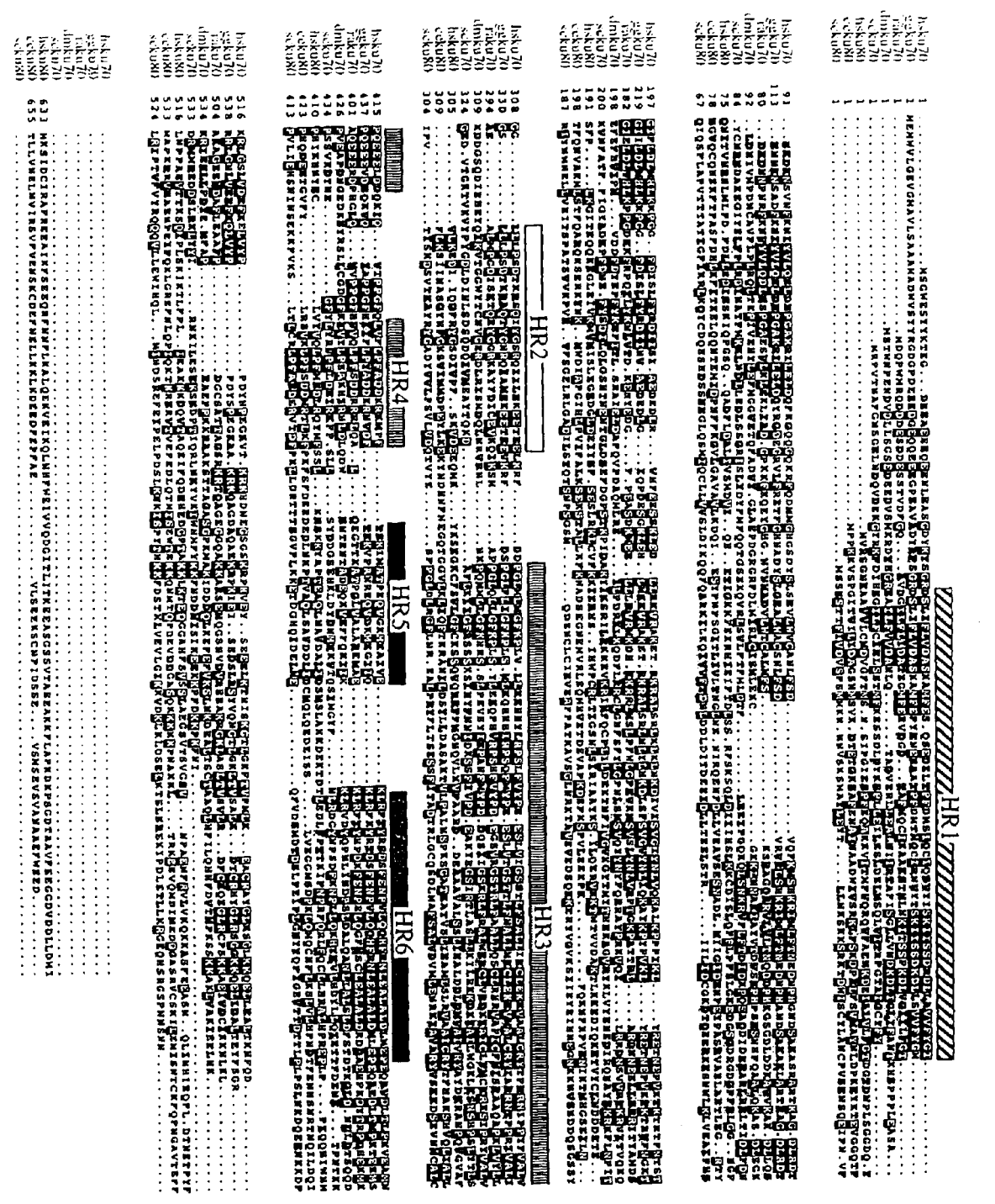

Sequence Analysis of Ku70 and Ku80 Indicates that They Are Structurally and Evolutionarily Related The inventors analysed the human Ku70 and Ku80 protein sequences (SEQ ID NOS:2 and 7) for candidate motifs involved in their interaction. They noted that the two subunits share regions of sequence similarity (a subset of which have been detected recently (Dynan and Yoo, 1998)) and that these similarities are shared by all the known homologues of Ku70 and Ku80. A Multiple Sequence Alignment of selected Ku70 and Ku80 sequences (SEQ ID NOS:2–9) was generated using the program "pileup" from the sequence analysis "Wisconsin Package, version 8.1" (Program Manual for the Wisconsin Package, Version 8, September 1994, Genetics Computer Group: Gap creation 3.00; Gap extension 0.10). The alignment is shown in FIG. 1: sequences from diverse branches of life were selected in order to give an indication of the most highly conserved regions, hence mouse or hamster homologues of Ku70 and Ku80 have not been included as these are almost identical to the human sequences.

Significantly, all of the Ku sequences align along their entire lengths, without necessitating the introduction of large gaps (the only notable exception to this occurs where the C-termini of the Caenorhabditis elegans and Human Ku80 sequences (SEQ ID NOS:7 and 8) extend beyond the other sequences; see below). Within the aligned region, the inventors established six segments of significant similarity between all of the Ku sequences, which they have designated Homology Regions 1–6 (HRs 1–6). These occur in the same order and with conserved spacing in each Ku sequence.

The features of the Ku70 and Ku80 sequences noted above suggest that these molecules fold into similar structures and may have evolved from a common ancestor. The HRs may correspond to conserved functional domains or structural features of the Ku70 and Ku80 polypeptides. Such regions could play key roles in specifying correct protein folding or mediating protein-protein and/or protein/nucleic acid interactions. Secondary structure predictions assign a high probability of a-helix formation within HRs 3, 5 and 6, and of β-strand formation in HR1. The short regions that separate HRs 2–6 are of variable length in the different proteins. These regions may correspond to inter-domain linkers or variable loops on the protein surface. Interestingly, within the region separating HR1 and HR2, there is very little similarity between the Ku70 and Ku80 sequences but there are several regions of sequence similarity exclusive to either the Ku70 or the Ku80 sequence families. Such regions could, therefore, specify Ku subunit-specific functions, although it is also possible that they share significant structural similarity with the other Ku subunit, but this is not easily detectable at the primary amino acid sequence level.

A second region exhibiting differences between the Ku70 and Ku80 sequences corresponds to the proteins' extreme C-termini. Thus, C. elegans and human Ku80 sequences (SEQ ID NOS:7 and 8) are considerably longer than other sequences in the alignment, and contain C-terminal extensions of 81 and 108 amino acid residues, respectively. The larger size of Ku80 compared to Ku70 is, therefore, largely due to the presence of a larger C-terminal domain (or an extra domain at the C-terminus). Throughout the present disclosure, this region is referred to as the Ku80 specific C-terminal extension (Ku80-CTE). The Ku70 sequences also share an exclusive extreme C-terminal sequence motif. The region that the inventors have identified as interacting with Ku70 in the 2-hybrid assay includes HR5 and HR6, making these attractive candidates for pseudo-homodimerisation interaction motifs.

Analysis of Regions of Ku80 Required for Heterodimerisation

The inventors tested a range of Ku80 deletion derivatives expressed as GST-fusions for their ability to interact with full-length Ku70. These derivatives and their relationships to the Ku80 homology regions are depicted in FIG. 2. The Ku80 derivatives were tested for an ability to affinity-purify full-length Ku70 from a crude bacterial extract, as described above. Briefly, GST-Ku80 derivatives were bound to glutathione agarose beads and incubated with biotinylated bacterial cell extracts containing full length Ku70. Proteins retained on the beads after seven washes in NETN buffer (20 mM Tris pH8.0, 150 mM KCL, 1 mM EDTA, 0.5% NP-40) were analysed by SDS-PAGE, western blotting and probing with HRP-conjugated streptavidin.

These binding studies revealed that Ku80ΔN1, Ku80ΔN2 and Ku80ΔN3 interact with Ku70, but Ku80ΔN3 interacts more strongly than the other two, larger, derivatives. These observations provide a potential explanation for why Ku80 derivatives longer than Ku80ΔN3 were not isolated in the 2-hybrid screen, and raise the possibility that sequences in HR3 and HR4 of Ku80 modulate the accessibility of the Ku70 interaction domain.

Notably, further N-terminal deletions of Ku80, represented by Ku80ΔN4 and Ku80ΔN5, reduce the binding of Ku70 to undetectable levels. Thus, residues in Ku80 HR5 are necessary for interaction with Ku70 in these assays. C-terminal Ku80 truncation derivatives were also tested. These analyses revealed that Ku80-CTE, the C-terminal region of human Ku80 that has no clear homology to Ku70, is not required for the Ku70 interaction. In contrast, further C-terminal deletion, represented by Ku80ΔN1C2, virtually eliminates Ku70 binding. Finally, a Ku80 derivative, Ku80ΔN3C1, which comprises only amino acid residues 439–592, is capable of binding Ku70 with high efficiency and specificity. These data reveal that the region of Ku80 comprising HR5 and HR6, together with an additional region between HR6 and the Ku80-CTE, mediates highly specific binding to Ku70.

Analysis of Regions of Ku70 Required for Heterodimerisation

Figure 3:
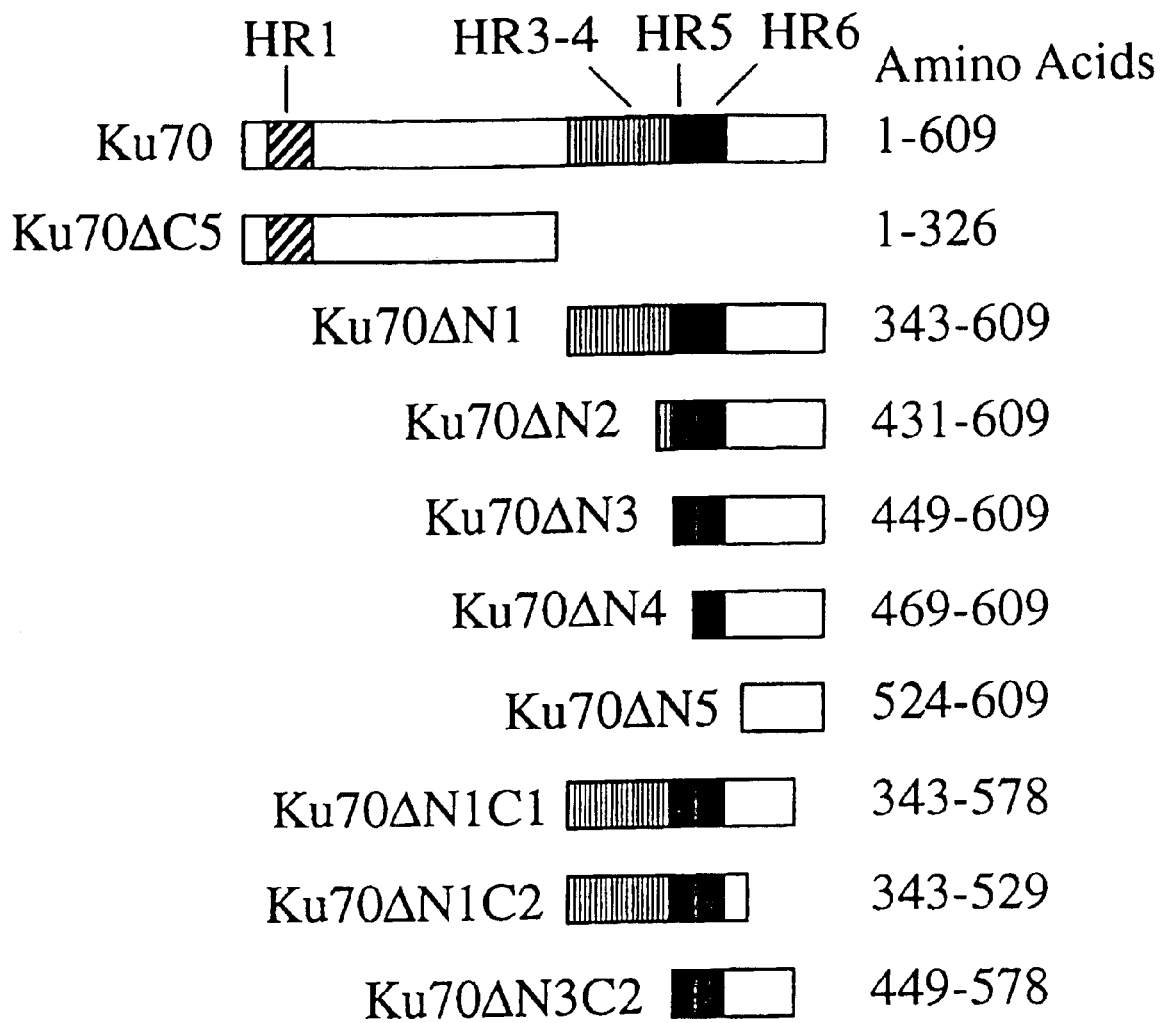
FIG. 3 shows the Ku70 deletion derivatives used to investigate the regions of Ku70 able to interact with full length Ku80. The deletion derivatives were expressed as GST fusion proteins. Full length Ku70 is represented by the uppermost bar. The positions of the Homology Regions (HRs) defined in FIG. 1 are indicated. For each HR, the shading is the same as used in FIG. 1. Deletion mutants are represented by shaded bars below this, drawn to scale with the numbers of the first and last amino acid residues of each deletion printed to the right of each bar.

The inventors generated a series of GST-Ku70 deletion mutants and tested their ability to affinity-purify Ku80 from a biotinylated crude bacterial cell lysate containing full-length Ku80. The Ku70 derivatives and their relationships to the Ku homology boxes are depicted in FIG. 3. Once again, GST-Ku70 derivatives were bound to glutathione agarose beads and incubated with biotinylated bacterial cell extracts containing full length Ku80. Proteins retained on the beads after seven washes in NETN buffer (20 mM Tris pH8.0, 150 mM KCL, 1 mM EDTA, 0.5% NP-40) were analysed by SDS-PAGE, western blotting and probing with HRP-conjugated streptavidin.

Full-length Ku70 binds to Ku80 efficiently, but does not interact with any of the other proteins present in crude bacterial extract. Whereas the N-terminal Ku70 region (Ku70ΔC5) that contains HR1 and HR2 displays very little binding to Ku80, the C-terminal region (Ku70ΔN1) containing HRs 3–6 binds Ku80 with high efficiency and specificity. Subdivision of Ku70ΔN1 allowed the interaction region of Ku70 to be further defined. Thus, whereas deletion of HR3 and HR4, exemplified by Ku70ΔN2 and Ku70ΔN3, has no discernible effect on Ku80 binding, further N-terminal deletion derivatives lacking HR5 or HRs 5 and 6 (Ku70ΔN4 and Ku70ΔN5, respectively) are totally abrogated for the Ku80 interaction.

C-terminal deletion of Ku70ΔN1 revealed that truncation of the final 31 amino acid residues has no discernible effect on Ku80 binding. This C-terminal region corresponds to a sequence motif that is apparently not present in *S. cerevisiae* Ku70 but exists in all other Ku70 homologues (FIG. 1), an observation which is consistent with the finding that this region does not function in Ku subunit interaction, and suggests a function for mammalian and arthropod Ku70 that does not exist in yeast. Any further deletion of the Ku70 C-terminus, however, leads to dramatic reduction in Ku80 binding.

Taken together, the above data indicate that a region of Ku70 containing HR5 and HR6, along with a third region of low Ku70/80 homology immediately C-terminal to HR6, is capable of binding to Ku80 with high specificity. It is striking that the interaction regions that the inventors have defined for both human Ku70 and Ku80 share significant similarities in sequence and position within the Ku polypeptides. The present disclosure therefore provides support for a model in which the Ku subunits interact by a pseudo-homodimerisation mechanism.

The present inventors have investigated Ku subunit interactions by generating untagged deletion derivatives of Ku70 and Ku80 using in vitro transcription and translation in rabbit reticulocyte lysate, followed by co-immunoprecipitation using antibodies specific for Ku70. These studies indicate that HR5 and HR6 are involved in the interaction, but show that a further 96 N-terminal amino acid residues, comprising HR3 and HR4, are also required in this system.

Ku80 Interacts Directly with DNA-PKcs

The inventors performed pull-down assays from HeLa cell nuclear extract using GST-Ku70 or GST-Ku80 bound to glutathione agarose beads. Thus, GST-Ku70 or GST-Ku80 protein was purified on glutathione agarose beads as described above, and the beads incubated with crude HeLa cell nuclear extract and washed extensively in buffer X containing 150 mM KCl. The bound proteins were then eluted in the presence of SDS, subjected to SDS-PAGE on a 6% polyacrylamide gel and detected by silver-staining. A control binding reaction was carried out using beads containing only GST.

Of the many proteins in the crude extract, DNA-PKcs is the only protein that is retrieved by affinity purification with either GST-Ku70 or GST-Ku80 beads (the identity of the retrieved species as DNA-PKcs was verified by quantitative western blot analyses). Indeed, other than proteins derived from the GST-Ku70 or GST-Ku80 preparations, DNA-PKcs is essentially the only polypeptide in the retrieved fractions. In contrast, DNA-PKcs is not recovered using beads containing GST alone.

The inventors investigated whether the observed interactions between DNA-PKcs and the individual Ku subunits were indirect and were being mediated by DNA and/or the Ku heterodimer present in the HeLa nuclear extract. EtBr was used in a final concentration of 0.2 mg/ml in order to address the potential involvement of DNA (EtBr disrupts protein-DNA interactions). Notably, the interaction between Ku80 and DNA-PKcs is unaffected by EtBr, suggesting that it is either direct or is mediated via a protein-protein interaction that does not require DNA. In contrast, the interaction between DNA-PKcs and Ku70 is essentially abolished by EtBr treatment, indicating that the interaction between Ku70 and DNA-PKcs is dependent upon protein-DNA interactions.

The inventors carried out binding reactions using an essentially homogeneous preparation of DNA-PKcs (this preparation was shown to contain Ku contamination at a level of around 1 in 840 DNA-PKcs molecules; see Materials and Methods). GST-Ku70 or GST-Ku80 containing glutathione agarose beads were incubated with 0.4 µg of purified DNA-PK$_{cs}$ under conditions of 120 mM KCl. The beads were then washed and any proteins retained on the beads were detected by silver-staining.

To investigate the effect of DNA upon these interactions binding reactions with purified DNA-PK$_{CS}$ were carried out in either in the presence of 20 ng/µl sonicated calf thymus DNA (which contains dsDNA ends and other discontinuities in the DNA double-helix and was shown to be highly effective at activating DNA-PK catalytic activity) or in the presence of 0.2 mg/ml EtBr. A control binding reaction using beads containing GST alone was also carried out.

Significantly, these studies revealed that GST-Ku80 interacts efficiently with purified DNA-PKcs and that this interaction is not affected by EtBr or by sheared genomic DNA. Furthermore, the inventors were unable to detect any endogenous Ku contamination in these Ku80 pull-downs using either polyclonal rabbit sera or monoclonal antibodies raised against the Ku subunits. Taken together, the data therefore reveal that there is a specific and direct interaction between Ku80 and DNA-PKcs, and eliminate the possibility that another protein species might be contributing to the interactions observed using the HeLa nuclear extract.

In contrast to the above results, very little interaction between Ku70 and purified DNA-PKcs was detected. Furthermore, no stimulation of binding was observed in the presence of DNA, arguing that the binding of GST-Ku70 to DNA-PKcs in the crude nuclear extract cannot be explained by DNA directly bridging between Ku70 and DNA-PKcs, nor by it inducing a conformational change in Ku70 or DNA-PKcs.

The inventors conducted assays with homogeneous DNA-PKcs and either GST-Ku70 or GST-Ku80 under conditions ranging from 50 mM to 150 mM KCl. These studies revealed that, at lower but not at higher ionic strengths, there is an interaction between Ku70 and DNA-PKcs. The interaction between DNA-PKcs and the Ku80 subunit, however, is much more salt stable and is still easily detectable at 150 mM KCl. Importantly, no significant interaction between GST and DNA-PKcs was observed at any salt concentration used, and the addition of DNA or EtBr had no affect on the binding of GST-Ku70 or GST-Ku80 under any of the conditions employed. The inventors conclude that there are contacts between each of the two Ku subunits and DNA-PKcs, but the contribution made by the Ku80 subunit is of greater strength and likely significance, given that it is the only interaction that can be detected at physiological salt concentrations.

The Ku80 C-terminal Region Interacts with DNA-PKcs

The inventors performed interaction assays with purified DNA-PKcs (to avoid the possible contribution of endogenous Ku or other protein species in nuclear extract) and a battery of Ku80 deletion derivatives that had been expressed as GST-fusion proteins and bound to the glutathione-agarose beads. Binding reactions and subsequent washes were carried out in NETN buffer (20 mM Hepes pH 7.5, 2 mM MgCl$_2$, 0.4% NP-40) containing 120 mM KCl to assay for the stronger, likely more physiological, binding observed between Ku80 and DNA-PKcs. Bound proteins were resolved on a 7% polyacrylamide gel and were detected by silver-staining. The Ku80 deletion derivatives used are shown in FIG. 4.

It was found that sequential deletions from the N-terminus of Ku80 (Ku80ΔN1–N6) have little of no effect on DNA-PKcs binding. Significantly, the smallest construct in this series, Ku80ΔN6, comprises amino acid residues 595–732 of Ku80 and corresponds to the C-terminal region of human Ku80, the Ku80-CTE, which has no homology to Ku70 sequences (see FIG. 1).

The expression construct encoding Ku80ΔN8 was designed to express only 22 amino acid residues corresponding to the extreme C-terminus of Ku80. Ku80ΔN7 and Ku80ΔN8 are still able to mediate an effective interaction with DNA-PKcs.

The inventors generated Ku80 derivatives representing a series of deletions from the C-terminus. These derivatives are shown in FIG. 4: they lack 0, 28, 70, 140, 202 or 267 amino acid residues from the C-terminus. Strikingly, removal of only 28 amino acid residues renders the resulting Ku80 derivative protein unable to bind DNA-PKcs.

Taken together, the data reveal that the interaction between human Ku80 and DNA-PKcs occurs through the Ku80-CTE region, and that the final 28 amino acid residues of Ku80 are necessary and sufficient for this interaction.

A Peptide from the Extreme C-terminus of Ku80 is Sufficient to Mediate Highly Specific and Efficient Interactions with DNA-PKcs The inventors synthesised a series of peptides (Peptides A–E, SEQ ID NOS:1 and 12–15) derived in sequence from the extreme C-terminus of Ku80 (residues 609 to 733, SEQ ID NO:11: see FIG. 5 and Materials and Methods). These peptides each contained 12 amino acid residues derived from overlapping sequence segments of Ku80, and have an N-terminal biotin moiety separated from the Ku80 derived sequence by the linker sequence Ser-Gly-Ser-Gly (SEQ ID NO:10). Each peptide ($2 \times 10^{-11}$ moles) was incubated with homogenous preparation DNA-PKcs ($1 \times 10^{-12}$ moles) in either Z' buffer containing 50 mM KCl or Z' buffer containing 100 mM KCl. The inventors then added paramagnetic beads conjugated with streptavidin to capture the peptide via the biotin-streptavidin interaction. The beads were recovered using a magnet, washed extensively in buffer containing the same concentration of KCl as the incubation buffer X (25 mM HEPES pH 7.5, 50 mM/100 mM KCl, 2 mM MgCl$_2$, 0.4% NP-40), and the bound protein eluted in SDS-PAGE sample buffer, resolved on a 6% polyacrylamide gel and detected using silver-staining.

Peptide E (SEQ ID NO:1), comprising the final 12 amino acid residues at the C-terminus of Ku80, interacts directly with DNA-PKcs at both 50 mM and 100 mM KCl. In contrast, none of the other peptides (Peptides A–D, SEQ ID NOS:12–15) exhibit significant DNA-PKcs binding.

The ability of each of the five peptides to retrieve proteins from a crude unfractionated HeLa cell nuclear extract was determined. Each peptide was incubated with 100 mg of HeLa nuclear extract in 50 mM Z' buffer, followed by capture of the peptide onto streptavidin-conjugated magnetic beads and subsequent washing in buffer X containing 50 mM KCl. Any proteins remaing bound to the peptide/ beads was eluted in SDS-PAGE buffer, resolved on a 6% polyacrylamide gel and detected with silver-staining. A control binding reaction was carried out with beads alone.

Strikingly, Peptide E (SEQ ID NO:1) affinity purified predominantly a single protein species of high molecular weight. This retrieved protein was confirmed to be DNA-PKcs by quantitative western blotting. Furthermore, western blotting revealed that the faint bands seen at around 150 kDa and 105 kDa correspond to breakdown products of DNA-PKcs. Additional studies have shown that Peptide E (SEQ ID NO:1) is able to deplete 60–70% of DNA-PKcs from HeLa nuclear extract, but that some DNA-PKcs always remains unbound, and that both DNA-PKcs affinity purified on Peptide E and that remaining in the extract display DNA-end stimulated kinase activity upon addition of purified Ku. In contrast, Peptides A–D (SEQ ID NOS:12 to 15) and a variety of control peptides all fail to specifically retrieve any proteins from nuclear extract.

Taken together, these results demonstrate that the extreme C-terminal 12 amino acid residues of Ku80 are sufficient to mediate a highly specific interaction with DNA-PKcs.

DISCUSSION

The present disclosure shows that Ku70 and Ku80 share considerable amino acid sequence similarity, suggesting that these two proteins have similar structures. Moreover, the inventors have have identified a region in Ku70 (amino acid residues 449–578) and one in Ku80 (residues 439–592) that mediate contacts within the Ku heterodimer. Strikingly, the regions of Ku70 and Ku80 that interact with one another share sequence homologies (HR5 and HR6; see FIG. 1) and are therefore predicted to be analogous structures. These data strongly suggest that the Ku subunits interact with one another through a pseudo-homodimerisation mechanism.

There is good agreement between the results presented herein and those of other researchers regarding the N-terminal boundary of the Ku subunit interaction domains (Osipovich et al., 1997; Wang et al., 1998a; Wu and Lieber, 1996). Furthermore, the C-terminal boundaries for the interaction domains have been located previously to amino acid residue 531 of human Ku80 (Osipovich et al., 1997) and residue 519 of human Ku70 (Cary et al., 1998)—in each case, these lie directly C-terminal to HR6. The data of the present inventors, however, indicate that other residues C-terminal to HR6 are also required for effective Ku70-Ku80 binding. Importantly, the results of previous point-mutational and functional analyses of the Ku subunits (Jin, S. F., et al. (1997) Embo Journal 16, 6874–6885) retrospectively provide significant support for the homologies between Ku70 and Ku80 being of functional significance (Jin and Weaver, 1997). Thus, mutation of residues that are highly conserved in our sequence analyses tend to abrogate Ku function, whereas mutation of those that are not conserved largely have little or no effect.

By generating untagged deletion derivatives of Ku70 and Ku80 using in vitro transcription and translation in rabbit reticulocyte lysate, followed by co-immunoprecipitation using antibodies specific for Ku70 the present inventors have confirmed that HR5 and HR6 are involved in effective interaction of the Ku subunits. These studies further revealed that a further 96 N-terminal amino acid residues, comprising HR3 and HR4, are required in this system. In this connection, it is noteworthy that Cary et. al. have reported that the Ku80 dimerisation domain maps to a central region of the protein (aa241–555: Cary et al., 1998), and that this region contains HR3 and HR4, in addition to HR5 and HR6. From FIG. 1 it is clear that HR3 and HR4 comprise the region that is most highly conserved between Ku70 and Ku80. This raises the possibility that HR3 and HR4 form a structural core within the Ku70-Ku80 heterodimer which is required for effective interactions between untagged derivatives of Ku70 or Ku80, but not when such derivatives are expressed fused to other structural motifs (GST or certain 2-hybrid fusion domains).

Previous studies have provided little information about the interaction of Ku with DNA-PKcs. The data presented herein demonstrate that both Ku80 and Ku70 are independently able to interact with DNA-PKcs, although the Ku80 interaction is much stronger at physiologically-relevant salt concentrations. Furthermore, the inventors have shown that the major DNA-PKcs binding domain of Ku80 is located at the extreme C-terminus of the molecule, and that the final C-terminal 12 amino acid residues of Ku80 are sufficient to mediate this highly specific interaction. This interaction is however weaker than that observed with a slightly larger C-terminal Ku80 fragment, suggesting that further residues in the Ku80-CTE might be required to mediate full-strength DNA-PKcs binding.

There are several lines of evidence to support the relevance of the Ku80-DNA-PKcs interaction disclosed herein in vivo. First, binding occurs under ionic conditions that are close to physiological. Second, this interaction is much stronger than the binding of DNA-PKcs to any other region of either Ku subunit, and the inventors have been unable to detect binding of DNA-PKcs to other control proteins or peptides. Third, the interaction between DNA-PKcs the C-terminal region of Ku80, either expressed as a GST fusion or presented as a biotinylated peptide, is highly selective, and can be used to affinity-purify DNA-PKcs to virtual homogeneity in one step from crude unfractionated human nuclear extract.

Perhaps surprisingly, GST-Ku80 and GST-Ku80 derivatives containing the C-terminal interaction domain identified by the present inventors bind to DNA-PKcs independently of dsDNA ends. This contrasts with the interaction between the native Ku heterodimer and DNA-PKcs, which only occurs in the presence of DNA (Gottlieb and Jackson, 1993; Suwa et al., 1994). Although other possibilities exist, one model to explain this difference is that the DNA-PKcs interaction region of Ku80 is masked in the native Ku heterodimer and only becomes exposed when a conformational change takes place upon DNA binding.

An exciting aspect arising from the work present herein is that DNA-PKcs-binding peptides, e.g. Peptide E (EGGDVDDLLDMI)(SEQ ID NO:1), can function as specific inhibitors of DNA-PK by blocking the interaction between the Ku heterodimer and DNA-PKcs. There are currently a number of compounds, such as Wortmannin and LY294002, that specifically inhibit members of the PIKL protein kinase and PI3-kinase families but until now there were no inhibitors specific for DNA-PKcs.

The sequence analysis shows that Ku80 and Ku70 differ dramatically at their C-termini. Ku80 homologues contain a C-terminal extension (CTE) region and Ku70 homologues appear to have a small Ku70-specific C-terminal region (See FIG. 1). These Ku subunit-specific regions appear not to participate in homodimerisation or DNA-binding and are presumably either modifications of the ancestral C-terminal domain, or additional protein domains. Consistent with this, the location of the DNA-PKcs interaction site in the Ku80-CTE suggests that the C-terminal domains form structures that are exposed on the surface of the Ku heterodimer, and hence this region of the protein can evolve an additional functionality to the Ku heterodimer without deleteriously affecting the DNA-binding function.

Considering that the final 12 residues of Ku80 are making contacts with DNA-PKcs, the large size of the Ku80-CTE in human Ku80 may allow Ku to overcome the steric hindrance which may inherently be a problem in interacting with a protein the size of DNA-PKcs. A second explanation may involve the modulation of DNA-PKcs binding by conformational change of the Ku80-CTE upon DNA-binding (see above). Alternatively the Ku80CTE (and also the Ku70-specific C-terminal region) may be the site of other protein-protein interactions. For example, it is noteworthy that, although lacking the DNA-PKcs interaction motif, C.

*elegans* Ku80 does possess a CTE, and this has several regions of homology with the Ku80 CTEs of mammals. It is tempting to speculate that these regions contact other proteins involved in DNA DSB repair or DNA damage signalling, or play roles in additional functions that have been ascribed to Ku, such as regulating telomeric functions and controlling chromatin structure (Featherstone and Jackson, 1999; Smith and Jackson, 1999). Analyses of the Ku70 and Ku80 CTEs, and the other homology regions of these two proteins that we have identified, are likely to be instrumental in furthering the understanding of the functions of Ku in these important processes.

The Ku heterodimer exists in cells from many organisms, including mammals, flies, nematode worms and yeast. However, no clear Ku homologues exist in the fully sequences genomes of various Bacteria and Archaea. This suggests that Ku evolved subsequently to the divergence of the eukaryotic and prokaryotic lineages, and clear sequence similarities between the Ku70 and Ku80 proteins strongly suggest they arose by a gene duplication and were already present in the last common ancestor of *S cerevisiae* and metazoa (it seems likely, therefore, that Ku homologues will also exist in metazoan plants).

For DNA-PKcs, however, the situation is somewhat different; genes for DNA-PKcs orthologues have been found in human, mouse, hamster, horse and *Xenopus laevis* (Dynan and Yoo, 1998) but are not evident in *S. cerevisiae*, nor in the virtually complete genome sequence of *C. elegans*. Significantly, the presence or absence of DNA-PKcs is mirrored by the state of the C-terminus of Ku80 in these organisms. Thus, the final 12 amino acid residues of human Ku80 that we have identified as interacting with DNA-PKcs are strikingly conserved in mouse and hamster Ku80 and these residues are absent from the *C. elegans* and *S. cerevisiae* Ku80 (or *S. cerevisiae* Ku70) homologues.

Furthermore the inventors have identified an open reading frame in the DNA database encoding a putative homologue of Ku80 from Drosophila that also lacks a DNA-PKcs interaction motif, highly suggestive that DNA-PK is absent from Drosophila. Hence, the first known occurrence of DNA-PKcs in evolution is in the vertebrates.

The above observations suggest that the DNA-PK enzyme has evolved to function in DNA DSB repair by hijacking an existing component of the Non-homologous end-joining (NHEJ) machinery, namely Ku, and hence adding to, or altering the functions that Ku can play in DNA repair. The function of Ku in NHEJ is conserved from yeast to humans but is only one of the two known pathways for the repair of DNA DSBs, the second mechanism being homologous recombination with an undamaged DNA strand.

All organisms studied appear to have the machinery for both NHEJ and homologous recombination (Critchlow, S. E., et al (1998) TIBS 23, 394–398, and references cited therein) however there is a distinct difference in the preference for these two DNA repair alternatives between yeast and humans. Yeast predominantly utilise homologous recombination whereas mammalian cells favour NHEJ. Although the high efficiency of NHEJ in Xenopus is well documented, the relative importance of NHEJ and recombination in this and other organisms is less well studied than in yeast or man. There is at least a correlation between the existance of DNA-PKcs in mammalian cells and a switch to NHEJ as the major pathway of DNA DSB repair.

Although it is true that NHEJ and homologous recombination are both used for the repair of randomly generated DNA damage, the process of V(D)J recombination, which involves creation of dsDNA breaks at specific sites in the immunoglobulin gene loci, only occurs through a mechanism of direct end joining. DNA-PK is required for V(D)J recombination and evolution of DNA-PK may reflect the requirement for the specific direct end-joining activity required in the generation of antibody diversity. Perhaps the specialisation of DNA-repair machinery of vertebrate cells for this specific form of direct end joining resulted in a general reduction of homologous recombination mechanisms in favour of NHEJ, or perhaps V(D)J recombination was able to develop due to the ability of cells to efficiently perform NHEJ. It has been suggested that the mechanism of V(D)J recombination has arrisen after the divergence of the jawed and jawless vertebrates due to the insertion of a transposable element, that encoded the ancestral RAG1/RAG2 genes, into an ancestral receptor gene resembeling the immunoglobulin and T-cell receptor genes found in present day jawed vertebrates. Hence it would be interesting to determine the time of appearance of the DNA-PKcs gene with respect to this event.

REFERENCES

Baumann and West (1998) *Proceedings Of the National Academy Of Sciences Of the United States Of America*, 95, 14066–14070.

Blier et al., (1993) *Journal Of Biological Chemistry*, 268, 7594–7601.

Bogue et al., (1998) *Proceedings Of the National Academy Of Sciences Of the United States Of America*, 95, 15559–15564.

Boulton and Jackson (1996a) *Nucleic Acids Research*, 24, 4639–4648.

Boulton and Jackson (1996b) *Embo Journal*, 15, 5093–5103.

Boulton and Jackson (1998) *Embo Journal*, 17, 1819–1828.

Cary et al., (1998) *Nucleic Acids Research*, 26, 974–979.

Cary et al., (1997) *Proceedings Of the National Academy Of Sciences Of the United States Of America*, 94, 4267–4272.

Chan and Leesmiller (1996) *Journal Of Biological Chemistry*, 271, 8936–8941.

Chou et al., (1992) *Journal Of Experimental Medicine*, 175, 1677–1684.

Critchlow and Jackson (1998) *Trends In Biochemical Sciences*, 23, 394–398.

Devries et al., (1989) *Journal Of Molecular Biology*, 208, 65–78.

Dvir et al., (1992) *Proceedings Of the National Academy Of Sciences Of the United States Of America*, 89, 11920–11924.

Dynan and Yoo (1998) *Nucleic Acids Research*, 26, 1551–1559.

Falzon et al., (1993) *Journal Of Biological Chemistry*, 268, 10546–10552.

Featherstone and Jackson (1999) *Mutation Research—DNA repair*, in press.

Finnie et al., (1995) *Proceedings Of the National Academy Of Sciences Of the United States Of America*, 92, 320–324.

Giffin et al., (1996) *Nature*, 380, 265–268.

Gottlieb and Jackson (1993) *Cell*, 72, 131–142.

Gu et al., (1996) *Journal Of Biological Chemistry*, 271, 19660–19663.

Gu et al., (1998) *Biochemistry*, 37, 9827–9835.

Gu et al., (1997) *Proceedings Of the National Academy Of Sciences Of the United States Of America*, 94, 8076–8081.

Hammarsten and Chu (1998) *Proceedings Of the National Academy Of Sciences Of the United States Of America*, 95, 525–530.

Hartley et al., (1995) *Cell*, 82, 849–856.
Jin and Weaver (1997) *Embo Journal*, 16, 6874–6885.
Kirchgessner et al., (1995) *Science*, 267, 1178–1183.
Koike et al., (1998) *Biochemical and Biophysical Research Communications*, 252, 679–685.
Lai and Herr (1992) *Proceedings Of the National Academy Of Sciences Of the United States Of America*, 89, 6958–6962.
Leesmiller et al., (1995) *Science*, 267, 1183–1185.
Mimori and Hardin (1986) *Journal Of Biological Chemistry*, 261, 375–379.
Oettinger et al., (1990) *Science*, 248, 1517–1523.
Osipovich et al., (1997) *Journal Of Biological Chemistry*, 272, 27259–27265.
Paillard and Strauss (1991) *Nucleic Acids Research*, 19, 5619–5624.
Porter et al., (1996) *Nucleic Acids Research*, 24, 582–585.
Schatz et al., (1989) *Cell*, 59, 1035–1048.
Siede et al., (1996) *Genetics*, 142, 91–102.
Singleton et al., (1999) *Molecular and Cellular Biology*, in press.
Sipley et al., (1995) *Proceedings Of the National Academy Of Sciences Of the United States Of America*, 92, 7515–7519.
Smith and Jackson (1999) *Genes and Development*, submitted.
Suwa et al., (1994) *Proceedings Of the National Academy Of Sciences Of the United States Of America*, 91, 6904–6908.
Taccioli et al., (1994) *Science*, 265, 1442–1445.
Wang et al., (1998a) *Journal Of Biological Chemistry*, 273, 842–848.
Wang et al., (1998b) *Journal Of Biological Chemistry*, 273, 31068–31074.
Wang et al., (1994) *Febs Letters*, 351, 219–224.
Wu and Lieber (1996) *Molecular and Cellular Biology*, 16, 5186–5193.
Yaneva et al., (1997) *Embo Journal*, 16, 5098–5112.
Zhu et al., (1996) *Cell*, 86, 379–389.

What is claimed is:

1. A screening method for identifying or obtaining a binding partner of Ku70 or Ku80, said method comprising;

(a) bringing a test binding partner into contact with one or more peptides consisting of an amino acid sequence selected from the group consisting of residues 36 to 90 of SEQ ID NO:2, residues 310 to 336 of SEQ ID NO:2, residues 343 to 422 of SEQ ID NO:2, residues 434 to 448 of SEQ ID NO:2, residues 449 to 467 of SEQ ID NO:2, residues 469–500 of SEQ ID NO:2, residues 57 to 112 of SEQ ID NO:3, residues 332 to 358 of SEQ ID NO:3, residues 365 to 444 of SEQ ID NO:3, residues 456 to 470 of SEQ ID NO:3, residues 471 to 489 of SEQ ID NO:3, residues 491 to 522 of SEQ ID NO:3, residues 27 to 79 of SEQ ID NO:4, residues 296 to 322 of SEQ ID NO:4, residues 329 to 408 of SEQ ID NO:4, residues 420 to 434 of SEQ ID NO:4, residues 437 to 455 of SEQ ID NO:4, residues 457 to 488 of SEQ ID NO:4, residues 32 to 80 of SEQ ID NO:5, residues 321 to 347 of SEQ ID NO:5, residues 354 to 433 of SEQ ID NO:5, residues 449 to 463 of SEQ ID NO:5, residues 468 to 486 of SEQ ID NO:5, residues 488 to 519 of SEQ ID NO:5, residues 30 to 83 of SEQ ID NO:6, residues 335 to 360 of SEQ ID NO:6, residues 361 to 441 of SEQ ID NO:6, residues 446 to 459 of SEQ ID NO:6, residues 464 to 482 of SEQ ID NO:6, residues 490 to 521 of SEQ ID NO:6, residues 8 to 61 of SEQ ID NO:7, residues 305 to 328 of SEQ ID NO:7, residues 338 to 417 of SEQ ID NO:7, residues 421 to 435 of SEQ-I-D NO:7, residues 441 to 459 of SEQ ID NO:7, residues 473 to 504 of SEQ ID NO:7, residues 9 to 63 of SEQ ID NO:8, residues 309 to 335 of SEQ ID NO:8, residues 349 to 430 of SEQ ID NO:8, residues 436 to 450 of SEQ ID NO:8, residues 460 to 478 of SEQ ID NO:8, residues 490 to 517 of SEQ ID NO:8, residues 4 to 53 of SEQ ID NO:9, residues 307 to 333 of SEQ ID NO:9, residues 340 to 420 of SEQ ID NO:9, residues 433 to 447 of SEQ ID NO:9, residues 457 to 475 of SEQ ID NO:9, residues 477 to 508 of SEQ ID NO:9, and EGGDVDDLLDMI (SEQ ID NO:1), and (b) determining binding of the test binding partner to one or more of said peptides, thereby identifying or obtaining a binding partner of Ku70 or Ku80.

2. A method of screening for an agent which modulates interaction between Ku70 and Ku80 and a binding partner, comprising, (a) bringing a test binding partner into contact with one or more peptides consisting of an amino acid sequence selected from the group consisting of residues 36 to 90 of SEQ ID NO:2, residues 310 to 336 of SEQ ID NO:2, residues 343 to 422 of SEQ ID NO:2, residues 434 to 448 of SEQ ID NO:2, residues 449 to 467 of SEQ ID NO:2, residues 469–500 of SEQ ID NO:2, residues 57 to 112 of SEQ ID NO:3, residues 332 to 358 of SEQ ID NO:3, residues 365 to 444 of SEQ ID NO:3, residues 456 to 470 of SEQ ID NO:3, residues 471 to 489 of SEQ ID NO:3, residues 491 to 522 of SEQ ID NO:3, residues 27 to 79 of SEQ ID NO:4, residues 296 to 322 of SEQ ID NO:4, residues 329 to 408 of SEQ ID NO:4, residues 420 to 434 of SEQ ID NO:4, residues 437 to 455 of SEQ ID NO:4, residues 457 to 488 of SEQ ID NO:4, residues 32 to 80 of SEQ ID NO:5, residues 321 to 347 of SEQ ID NO:5, residues 354 to 433 of SEQ ID NO:5, residues 449 to 463 of SEQ ID NO:5, residues 468 to 486 of SEQ ID NO:5, residues 488 to 519 of SEQ ID NO:5, residues 30 to 83 of SEQ ID NO:6, residues 335 to 360 of SEQ ID NO:6, residues 361 to 441 of SEQ ID NO:6, residues 446 to 459 of SEQ ID NO:6, residues 464 to 482 of SEQ ID NO:6, residues 490 to 521 of SEQ ID NO:6, residues 8 to 61 of SEQ ID NO:7, residues 305 to 328 of SEQ ID NO:7, residues 338 to 417 of SEQ ID NO:7, residues 421 to 435 of SEQ-I-D NO:7, residues 441 to 459 of SEQ ID NO:7, residues 473 to 504 of SEQ ID NO:7, residues 9 to 63 of SEQ ID NO:8, residues 309 to 335 of SEQ ID NO:8, residues 349 to 430 of SEQ ID NO:8, residues 436 to 450 of SEQ ID NO:8, residues 460 to 478 of SEQ ID NO.8, residues 490 to 517 of SEQ ID NO:8, residues 4 to 53 of SEQ ID NO:9, residues 307 to 333 of SEQ ID NO:9, residues 340 to 420 of SEQ ID NO:9, residues 433 to 447 of SEQ ID NO:9, residues 457 to 475 of SEQ ID NO:9, residues 477 to 508 of SEQ ID NO:9, and EGGDVDDLLDMI (SEQ ID NO:1), and in the presence of a test agent;

(b) determining binding of said one or more peptides to the binding partner, thereby screening for an agent which modulates interaction between Ku70 and Ku80 and a binding partner.

3. A screening method according to claim 1 or 2 wherein said binding partner or said test agent is a polypeptide having a amino acid sequence which shares at least 50% homology with DNA-PK$_{cs}$.

4. A screening or assay method according to claim 1 or 2 including purifying and/or isolating a test agent or a test binding partner from a mixture or extract.

5. A screening or assay method according to claim 1 or 2 including determining the ability of one or more fractions of a test mixture or extract to bind to one or more of said peptides.

6. A method according to claim 1 or 2 comprising labelling one of said test agent or said binding partner and said peptide with a detectable label, immobilising the other on a solid support and bringing the test binding partner or test agent and the peptide into contact.

7. A method according to claim 1 or 2 wherein said binding partner or said agent is in a test sample.

8. A method according to claim 7 including quantifying the amount of the agent or binding partner in the sample.

9. A method of determining the presence in a test sample of an agent or binding partner which has the ability to bind Ku70 or Ku80, the method comprising:

(a) bringing a test binding partner into contact with one or more peptides consisting of an amino acid sequence selected from the group consisting of residues 36 to 90 of SEQ ID NO:2, residues 310 to 336 of SEQ ID NO:2, residues 343 to 422 of SEQ ID NO:2, residues 434 to 448 of SEQ ID NO:2, residues 449 to 467 of SEQ ID NO:2, residues 469–500 of SEQ ID NO:2, residues 57 to 112 of SEQ ID NO:3, residues 332 to 358 of SEQ ID NO:3, residues 365 to 444 of SEQ ID NO:3, residues 456 to 470 of SEQ ID NO:3, residues 471 to 489 of SEQ ID NO:3, residues 491 to 522 of SEQ ID NO:3, residues 27 to 79 of SEQ ID NO:4, residues 296 to 322 of SEQ ID NO:4, residues 329 to 408 of SEQ ID NO:4, residues 420 to 434 of SEQ ID NO:4, residues 437 to 455 of SEQ ID NO:4, residues 457 to 488 of SEQ ID NO:4, residues 32 to 80 of SEQ ID NO:5, residues 321 to 347 of SEQ ID NO:5, residues 354 to 433 of SEQ ID NO:5, residues 449 to 463 of SEQ ID NO:5, residues 468 to 486 of SEQ ID NO:5, residues 488 to 519 of SEQ ID NO:5, residues 30 to 83 of SEQ ID NO:6, residues 335 to 360 of SEQ ID NO:6, residues 361 to 441 of SEQ ID NO:6, residues 446 to 459 of SEQ ID NO:6, residues 464 to 482 of SEQ ID NO:6, residues 490 to 521 of SEQ ID NO:6, residues 8 to 61 of SEQ ID NO:7, residues 305 to 328 of SEQ ID NO:7, residues 338 to 417 of SEQ ID NO:7, residues 421 to 435 of SEQ-I-D NO:7, residues 441 to 459 of SEQ ID NO:7, residues 473 to 504 of SEQ ID NO:7, residues 9 to 63 of SEQ ID NO:8, residues 309 to 335 of SEQ ID NO:8, residues 349 to 430 of SEQ ID NO:8, residues 436 to 450 of SEQ ID NO:8, residues 460 to 478 of SEQ ID NO:8, residues 490 to 517 of SEQ ID NO:8, residues 4 to 53 of SEQ ID NO:9, residues 307 to 333 of SEQ ID NO:9, residues 340 to 420 of SEQ ID NO:9, residues 433 to 447 of SEQ ID NO:9, residues 457 to 475 of SEQ ID NO:9, residues 477 to 508 of SEQ ID NO:9, and EGGDVDDLLDMI (SEQ ID NO:1), and determining binding of the test sample to one or more of said peptides, thereby determining the presence in the test sample of an agent or binding partner which has the ability to bind Ku70 or Ku80.

10. A method of determining the presence in a test sample of a Ku70 or Ku80, the method comprising:

(a) bringing a test binding partner into contact with one or more peptides consisting of an amino acid sequence selected from the group consisting of residues 36 to 90 of SEQ ID NO:2, residues 310 to 336 of SEQ ID NO:2, residues 343 to 422 of SEQ ID NO:2, residues 434 to 448 of SEQ ID NO:2, residues 449 to 467 of SEQ ID NO:2, residues 469–500 of SEQ ID NO:2, residues 57 to 112 of SEQ ID NO:3, residues 332 to 358 of SEQ ID NO:3, residues 365 to 444 of SEQ ID NO:3, residues 456 to 470 of SEQ ID NO:3, residues 471 to 489 of SEQ ID NO:3, residues 491 to 522 of SEQ ID NO:3, residues 27 to 79 of SEQ ID NO:4, residues 296 to 322 of SEQ ID NO:4, residues 329 to 408 of SEQ ID NO:4, residues 420 to 434 of SEQ ID NO:4, residues 437 to 455 of SEQ ID NO:4, residues 457 to 488 of SEQ ID NO:4, residues 32 to 80 of SEQ ID NO:5, residues 321 to 347 of SEQ ID NO:5, residues 354 to 433 of SEQ ID NO:5, residues 449 to 463 of SEQ ID NO:5, residues 468 to 486 of SEQ ID NO:5, residues 488 to 519 of SEQ ID NO:5, residues 30 to 83 of SEQ ID NO:6, residues 335 to 360 of SEQ ID NO:6, residues 361 to 441 of SEQ ID NO:6, residues 446 to 459 of SEQ ID NO:6, residues 464 to 482 of SEQ ID NO:6, residues 490 to 521 of SEQ ID NO:6, residues 8 to 61 of SEQ ID NO:7, residues 305 to 328 of SEQ ID NO:7, residues 338 to 417 of SEQ ID NO:7, residues 421 to 435 of SEQ-I-D NO:7, residues 441 to 459 of SEQ ID NO:7, residues 473 to 504 of SEQ ID NO:7, residues 9 to 63 of SEQ ID NO:8, residues 309 to 335 of SEQ ID NO:8, residues 349 to 430 of SEQ ID NO:8, residues 436 to 450 of SEQ ID NO:8, residues 460 to 478 of SEQ ID NO:8, residues 490 to 517 of SEQ ID NO:8, residues 4 to 53 of SEQ ID NO:9, residues 307 to 333 of SEQ ID NO:9, residues 340 to 420 of SEQ ID NO:9, residues 433 to 447 of SEQ ID NO:9, residues 457 to 475 of SEQ ID NO:9, residues 477 to 508 of SEQ ID NO:9, and EGGDVDDLLDMI (SEQ ID NO:1), and determining binding of the test sample to one or more of said peptides, thereby determining the presence in the test sample of a Ku70 or Ku80 in a test sample.

* * * * *

SEQUENCE LISTING

<160> NUMBER OF SEQ ID NOS: 18

<210> SEQ ID NO 1
<211> LENGTH: 12
<212> TYPE: PRT
<213> ORGANISM: Homo sapiens

<400> SEQUENCE: 1

Glu Gly Gly Asp Val Asp Asp Leu Leu Asp Met Ile
 1               5                  10

<210> SEQ ID NO 2
<211> LENGTH: 609
<212> TYPE: PRT
<213> ORGANISM: Homo sapiens

<400> SEQUENCE: 2

Met Ser Gly Trp Glu Ser Tyr Tyr Lys Thr Glu Gly Asp Glu Glu Ala
 1               5                   10                  15

Glu Glu Glu Gln Glu Glu Asn Leu Glu Ala Ser Gly Asp Tyr Lys Tyr
             20                  25                  30

Ser Gly Arg Asp Ser Leu Ile Phe Leu Val Asp Ala Ser Lys Ala Met
         35                  40                  45

Phe Glu Ser Gln Ser Glu Asp Glu Leu Thr Pro Phe Asp Met Ser Ile
     50                  55                  60

Gln Cys Ile Gln Ser Val Tyr Ile Ser Lys Ile Ile Ser Ser Asp Arg
 65                  70                  75                  80

Asp Leu Leu Ala Val Val Phe Tyr Gly Thr Glu Lys Asp Lys Asn Ser
                 85                  90                  95

Val Asn Phe Lys Asn Ile Tyr Val Leu Gln Glu Leu Asp Asn Pro Gly
            100                 105                 110

Ala Lys Arg Ile Leu Glu Leu Asp Gln Phe Lys Gly Gln Gln Gly Gln
        115                 120                 125

Lys Arg Phe Gln Asp Met Met Gly His Gly Ser Asp Tyr Ser Leu Ser
    130                 135                 140

Glu Val Leu Trp Val Cys Ala Asn Leu Phe Ser Asp Val Gln Phe Lys
145                 150                 155                 160

Met Ser His Lys Arg Ile Met Leu Phe Thr Asn Glu Asp Asn Pro His

-continued

```
                165                 170                 175
Gly Asn Asp Ser Ala Lys Ala Ser Arg Ala Arg Thr Lys Ala Gly Asp
            180                 185                 190
Leu Arg Asp Thr Gly Ile Phe Leu Asp Leu Met His Leu Lys Lys Pro
        195                 200                 205
Gly Gly Phe Asp Ile Ser Leu Phe Tyr Arg Asp Ile Ser Ile Ala
    210                 215                 220
Glu Asp Glu Asp Leu Arg Val His Phe Glu Glu Ser Ser Lys Leu Glu
225                 230                 235                 240
Asp Leu Leu Arg Lys Val Arg Ala Lys Glu Thr Arg Lys Arg Ala Leu
                245                 250                 255
Ser Arg Leu Lys Leu Lys Leu Asn Lys Asp Ile Val Ile Ser Val Gly
            260                 265                 270
Ile Tyr Asn Leu Val Gln Lys Ala Leu Lys Pro Pro Ile Lys Leu
        275                 280                 285
Tyr Arg Glu Thr Asn Glu Pro Val Lys Thr Lys Thr Arg Thr Phe Asn
    290                 295                 300
Thr Ser Thr Gly Gly Leu Leu Pro Ser Asp Thr Lys Arg Ser Gln
305                 310                 315                 320
Ile Tyr Gly Ser Arg Gln Ile Ile Leu Glu Lys Glu Thr Glu Glu
                325                 330                 335
Leu Lys Arg Phe Asp Asp Pro Gly Leu Met Leu Met Gly Phe Lys Pro
            340                 345                 350
Leu Val Leu Leu Lys Lys His His Tyr Leu Arg Pro Ser Leu Phe Val
        355                 360                 365
Tyr Pro Glu Glu Ser Leu Val Ile Gly Ser Ser Thr Leu Phe Ser Ala
    370                 375                 380
Leu Leu Ile Lys Cys Leu Glu Lys Glu Val Ala Ala Leu Cys Arg Tyr
385                 390                 395                 400
Thr Pro Arg Arg Asn Ile Pro Pro Tyr Phe Val Ala Leu Val Pro Gln
                405                 410                 415
Glu Glu Glu Leu Asp Asp Gln Lys Ile Gln Val Thr Pro Pro Gly Phe
            420                 425                 430
Gln Leu Val Phe Leu Pro Phe Ala Asp Asp Lys Arg Lys Met Pro Phe
        435                 440                 445
Thr Glu Lys Ile Met Ala Thr Pro Glu Gln Val Gly Lys Met Lys Ala
    450                 455                 460
Ile Val Glu Lys Leu Arg Phe Thr Tyr Arg Ser Asp Ser Phe Glu Asn
465                 470                 475                 480
Pro Val Leu Gln Gln His Phe Arg Asn Leu Glu Ala Leu Ala Leu Asp
                485                 490                 495
Leu Met Glu Pro Glu Gln Ala Val Asp Leu Thr Leu Pro Lys Val Glu
            500                 505                 510
Ala Met Asn Lys Arg Leu Gly Ser Leu Val Asp Glu Phe Lys Glu Leu
        515                 520                 525
Val Tyr Pro Pro Asp Tyr Asn Pro Glu Gly Lys Val Thr Lys Arg Lys
    530                 535                 540
His Asp Asn Glu Gly Ser Gly Ser Lys Arg Pro Lys Val Glu Tyr Ser
545                 550                 555                 560
Glu Glu Glu Leu Lys Thr His Ile Ser Lys Gly Thr Leu Gly Lys Phe
                565                 570                 575
Thr Val Pro Met Leu Lys Glu Ala Cys Arg Ala Tyr Gly Leu Lys Ser
            580                 585                 590
```

```
Gly Leu Lys Lys Gln Glu Leu Leu Glu Ala Leu Thr Lys His Phe Gln
            595                 600                 605

Asp

<210> SEQ ID NO 3
<211> LENGTH: 632
<212> TYPE: PRT
<213> ORGANISM: Gallus gallus

<400> SEQUENCE: 3

Met Glu Met Trp Val Leu Gly Glu Val Gly Met Ala Val Leu Ser Ala
  1               5                  10                  15

Ala Ala Met Ala Asp Trp Val Ser Tyr Tyr Arg Gly Asp Gly Pro Asp
             20                  25                  30

Glu Glu Glu Asp Gly Glu Gln Gln Glu Glu Gly Pro Glu Ala Val
         35                  40                  45

Ala Asp Tyr Arg Phe Ser Arg Asp Ser Leu Ile Phe Leu Val Asp
     50                  55                  60

Ala Ser Lys Ala Met Phe Glu Pro Tyr Glu Asn Glu Ala Ala Thr
 65                  70                  75                  80

Pro Phe Asp Met Thr Met Gln Cys Ile Arg Asn Val Tyr Thr Ser Lys
                 85                  90                  95

Ile Ile Ser Ser Asp Lys Asp Leu Leu Ser Val Val Phe Tyr Gly Met
                100                 105                 110

Glu Asn Asn Lys Asn Ser Ala Asp Phe Lys His Ile Tyr Val Leu Gln
                115                 120                 125

Glu Leu Asp Asn Pro Gly Ala Lys Arg Ile Leu Glu Leu Asp Gln Tyr
            130                 135                 140

Arg Gly Asp Glu Gly Arg Val Leu Phe Arg Glu Thr Phe Gly His Asn
145                 150                 155                 160

Ala Asp Tyr Ser Leu Gly Glu Ala Leu Trp Ala Cys Ser Asn Leu Phe
                165                 170                 175

Ser Asp Val Arg Val Arg Leu Ser His Lys Arg Ile Met Leu Phe Thr
                180                 185                 190

Asn Glu Asp Asn Pro His Ala Asn Asp Ser Ala Lys Ala Lys Leu Ala
                195                 200                 205

Arg Thr Arg Ala Gly Asp Leu Arg Asp Thr Gly Ile Ile Leu Asp Leu
            210                 215                 220

Met His Leu Lys Lys Pro Gly Gly Phe Asp Ile Ser Leu Phe Tyr Arg
225                 230                 235                 240

Asp Ile Ile Asn Val Ala Glu Asp Glu Asp Leu Gly Ile Gln Pro Asp
                245                 250                 255

Glu Ser Gly Lys Leu Glu His Leu Met Lys Lys Val Arg Ala Lys Glu
                260                 265                 270

Thr Arg Lys Arg Ala Leu Ser Arg Leu Asn Leu Tyr Leu Asn Lys Asp
            275                 280                 285

Leu Ser Phe Ser Val Gly Val Tyr Asn Leu Ile Gln Lys Ala Tyr Lys
        290                 295                 300

Pro Tyr Pro Val Lys Leu Tyr Arg Glu Thr Asn Glu Pro Val Lys Thr
305                 310                 315                 320

Lys Thr Arg Val Phe Asn Gly Lys Thr Gly Ser Leu Leu Leu Pro Ser
                325                 330                 335

Asp Thr Lys Arg Ala Gln Thr Tyr Gly Asn Arg Gln Ile Ala Met Glu
            340                 345                 350
```

-continued

```
Lys Glu Glu Thr Glu Glu Val Lys Arg Phe Asp Ser Pro Gly Leu Phe
            355                 360                 365
Leu Ile Gly Phe Lys Pro Leu Ser Met Leu Lys Gln His His His Ile
            370                 375                 380
Arg Pro Ser Gln Phe Met Tyr Pro Glu Glu Ser Leu Val Thr Gly Ser
385                 390                 395                 400
Thr Thr Leu Phe Asn Ala Leu Leu Met Lys Cys Leu Glu Lys Glu Val
            405                 410                 415
Met Ala Leu Cys Arg Tyr Ile Ala Arg Arg Asn Thr Pro Pro Arg Ile
            420                 425                 430
Val Ala Leu Ile Pro Gln Glu Glu Val Asp Glu Gln Lys Val Gln
            435                 440                 445
Ile Ala Pro Pro Gly Phe His Ile Ile Phe Leu Pro Tyr Ala Asp Asp
            450                 455                 460
Lys Arg Asn Val Asp Phe Thr Glu Lys Val Pro Ala Asn Arg Glu Gln
465                 470                 475                 480
Val Asp Lys Met Lys Gly Ile Ile Gln Lys Leu Arg Phe Lys Tyr Arg
            485                 490                 495
Thr Asp Ser Phe Glu Asn Pro Val Leu Gln Gln His Phe Arg Asn Leu
            500                 505                 510
Glu Ala Leu Ala Leu Asp Met Leu Glu Pro Gln Ala Glu Asp Leu
            515                 520                 525
Thr Met Pro Lys Thr Glu Glu Met Ser Arg Arg Leu Gly Asn Leu Val
            530                 535                 540
Glu Glu Phe Lys Gln Leu Val Tyr Pro Pro Asp Tyr Ser Pro Glu Gly
545                 550                 555                 560
Lys Ala Ala Lys Arg Lys Gln Ala Gly Asp Ala Gln Ala Glu Lys Arg
            565                 570                 575
Pro Lys Ile Glu Ile Ser Glu Asp Ser Leu Arg Ser Tyr Val Gln Asn
            580                 585                 590
Gly Thr Leu Gly Lys Leu Thr Val Ser Ala Leu Lys Asp Thr Cys Arg
            595                 600                 605
His Tyr Gly Leu Arg Ser Gly Gly Lys Lys Gln Glu Leu Ile Asp Ala
            610                 615                 620
Leu Thr Glu Tyr Phe Ser Gly Arg
625                 630

<210> SEQ ID NO 4
<211> LENGTH: 600
<212> TYPE: PRT
<213> ORGANISM: Rhipicephalus appendiculatus

<400> SEQUENCE: 4

Met Asp Gln Pro Trp Met Arg Gln Asp Asp Glu Ser Asp Glu
1               5                   10                  15
Ser Ser Thr Val Asp Phe Gly Gln Ala Val Asp Gly Ile Leu Phe Leu
            20                  25                  30
Ile Asp Ala Thr Glu Gly Met Phe Glu Glu Val Asp Gly Asp Thr Ala
            35                  40                  45
Phe Met Gln Cys Ile Lys Ala Ala Lys Ser Thr Met Leu Asn Lys Ile
            50                  55                  60
Thr Ser Ser Pro Lys Asp Leu Val Gly Ile Ile Leu Phe Gly Thr Asp
65                  70                  75                  80
Lys Asp Asn Asn Pro Asn Arg Phe Lys Asn Val Tyr Val Leu Gln Asp
```

-continued

```
                     85                    90                    95
Leu Glu Ser Pro Gly Ala Glu Ser Val Leu Lys Leu Glu Lys Leu Ile
                100                   105                   110
Ala Asp Gly Pro Lys Lys Phe Lys Gln Glu Tyr Gly His Gly Asn Val
                115                   120                   125
Asn Met Ala Asp Val Leu Trp Thr Cys Ala Leu Met Phe Ser Lys Ser
            130                   135                   140
Arg Ala Gly Gln Arg Arg Val Leu Val Leu Thr Asn Gln Asp Asp Pro
145                   150                   155                   160
His Lys Gly Ser Gly Asp Leu Asp Lys Ala Val Val Lys Ala Lys
                165                   170                   175
Asp Leu Leu Gln Ser Gly Ile Glu Leu Asp Leu Val His Leu Lys Pro
                180                   185                   190
Pro Gly Asp Lys Lys Phe Arg Pro Gln Ile Leu Tyr Lys Asn Leu Val
                195                   200                   205
Thr Asp Lys Glu Asn Tyr Glu Asp Gly Phe Pro Glu Ala Ser Asp Lys
            210                   215                   220
Met Glu Glu Leu Leu Arg Val Arg Met Lys Asp His Lys Lys Arg
225                   230                   235                   240
Arg Leu Met Ser Leu Pro Phe Trp Leu Gly Pro Glu Val Lys Met Ser
                245                   250                   255
Val Ser Leu Tyr Asn Leu Val Arg Pro Thr Gly Lys Pro Ala Thr Thr
                260                   265                   270
Arg Leu Ala Arg Asp Asn Asn Glu Glu Leu Leu Ser Arg Arg Ile Thr
                275                   280                   285
Tyr Ala Met Asp Ser Ala Glu Ala Leu Met Pro Gly Asp Ile Ser Lys
            290                   295                   300
Thr Gln Glu Tyr Gly Gly Arg Lys Ala Tyr Phe Asp Ile Cys Glu Val
305                   310                   315                   320
Lys Gln Ile Lys Ser Met Ala Pro Pro Gly Leu Gln Leu Leu Gly Phe
                325                   330                   335
Lys Pro Leu Ser Tyr Leu Glu Lys Gln Pro His Val Arg Pro Ser His
                340                   345                   350
Phe Val Tyr Pro Asp Glu Gly Ser Val Arg Gly Ser Thr Arg Leu Phe
                355                   360                   365
Ala Ala Leu Leu Gln Ser Cys Leu Arg His Arg Val Ala Pro Ile Cys
            370                   375                   380
Phe Trp Ile Ser Arg Ala Ala Gln Ala Pro Lys Leu Val Tyr Leu Leu
385                   390                   395                   400
Ala Gln Glu Glu Arg Asp Pro His Gly Leu Gln Met Val Pro Pro
                405                   410                   415
Gly Phe His Val Val Gln Leu Pro Phe Ser Asp Asp Arg Arg Leu
                420                   425                   430
Gln Ala Leu Gln Glu Gly Thr Thr Lys Ala Thr Pro Gly Leu Val Ala
            435                   440                   445
Leu Ala Arg Glu Met Ala Glu Lys Leu Arg Phe Thr Tyr His Pro Asp
            450                   455                   460
Lys Phe Glu Asn Pro Glu Leu Gln Gly Phe Trp Ser Cys Leu Glu Ala
465                   470                   475                   480
Leu Ala Leu Asp Arg Asp Asp Ala Glu His Pro Lys Asp Tyr Thr Arg
                485                   490                   495
Pro Asp His Glu Lys Met Lys Ala Lys Ala Gly Glu Glu Met Asp Ala
                500                   505                   510
```

-continued

```
Phe Leu Glu Ala Ala Phe Pro Asp Gly Cys Ser Ala Thr Thr Ala Gly
            515                 520                 525

Ser Arg Lys Arg Thr Gln Ala Gly Glu Gly Gly Gln Ala Lys Lys Ala
        530                 535                 540

Arg Ser Glu Asn Gln Gly Ser Asn Val Asp Val Arg Glu Glu Ala Lys
545                 550                 555                 560

Arg Gly Lys Leu Ala Ser Leu Thr Val Ser Val Leu Arg Asp Phe Cys
                565                 570                 575

Lys Gln Glu Gly Leu Arg Cys Pro Ser Lys Lys Ala Glu Ile Val Asp
            580                 585                 590

Cys Ile Lys Lys His Leu Lys Leu
        595                 600

<210> SEQ ID NO 5
<211> LENGTH: 631
<212> TYPE: PRT
<213> ORGANISM: Drosophila melanogaster

<400> SEQUENCE: 5

Met Ser Thr Trp Asn Pro Glu Asn Asp Val Asp Leu Leu Ser Gly Ser
1               5                  10                  15

Glu Asp Glu Glu Asp Val Ser Met Lys Arg Asp Tyr His Gly Arg Glu
            20                  25                  30

Ala Ile Leu Phe Val Val Asp Ala Asn Leu Gln Thr Ala Gly Val Glu
        35                  40                  45

Arg Leu Leu Glu Ala Leu Asn Ile Ile Arg Thr Ala Phe Ile Ser Gly
    50                  55                  60

Leu Leu Val Asn Asp Lys Asp Leu Ile Gly Leu Ile Phe Ala Asn Thr
65                  70                  75                  80

Lys His Ser Pro Pro Pro Leu Glu Ala Ser Ala Leu Asp Asn Ile Val
                85                  90                  95

Met Pro Asp Asn Cys Ala Val Phe Leu Pro Leu Arg Gln Leu Thr Lys
            100                 105                 110

Pro Ile Val Glu His Tyr Leu Glu Phe Met Gly Val Glu Thr Gln
        115                 120                 125

Phe Ala Asp Val Tyr Gly Leu Ala Glu Pro Asp Gly Arg Gly Arg Phe
    130                 135                 140

Asp Leu Met Ile Arg Leu Cys Ile Glu Met Leu Glu Lys Cys Gly Lys
145                 150                 155                 160

Lys Leu Asn Asn Ala Lys Ile Ala Tyr Val Thr Asp Val Ser Glu Pro
                165                 170                 175

His Pro Ser Asn Ser Asn His Phe Gln Ala Ala Leu Gln Lys Ala Ser
            180                 185                 190

Asp Leu Glu Gly Lys Glu Phe Glu Phe His Val Ile Pro Met Val Asp
        195                 200                 205

Asp Phe Asp Tyr Glu Pro Phe Tyr Lys Glu Phe Ile Thr Leu Ser Arg
    210                 215                 220

Ala Ile Glu Leu Asp Ala Phe Gln Val Pro Asp Ala Gln Met Leu Arg
225                 230                 235                 240

Glu Ile Leu Pro Asp Arg Lys Leu Lys Gln Asp Phe Leu Arg Arg Cys
                245                 250                 255

Leu Gly His Phe Ser Phe Tyr Leu Gly Pro Asn Leu Ser Met Ser Val
            260                 265                 270

Gln Tyr Tyr Asn Tyr Phe Gln Arg Arg Ala Tyr Pro Arg Lys Val Gln
```

-continued

```
                275                 280                 285
Ile Leu Arg Arg Asp Asn Ser Val Val Arg Thr Lys Arg Val Ile Thr
            290                 295                 300
Val Gln Lys Gln Lys Asp Asp Gly Ser Gln Asp Ile Glu His Glu Tyr
305                 310                 315                 320
Gln Ile Lys Val Thr Gly Gly Trp Tyr Thr Cys Asn Val Gly Glu Arg
                325                 330                 335
Asp Leu Arg Ile Ser Met Asp Gln Leu Asn Arg Val Arg Asn Leu His
            340                 345                 350
Lys Pro Gln Met Met Leu Leu Gly Phe Lys His Arg Ser Ser Leu Pro
            355                 360                 365
Glu Val Ser Tyr Ile Lys Pro Ala Asn Phe Met Tyr Pro Asp Asp Gln
370                 375                 380
Ser Ile Ile Gly Ser Lys Arg Leu Phe Arg Ala Leu Trp Glu Arg Cys
385                 390                 395                 400
Leu Val Arg Asp Lys Ile Ala Ile Cys Leu Phe Met Cys Lys Arg Lys
                405                 410                 415
Ser Ile Pro Arg Tyr Val Ala Leu Val Pro Val Glu Ala Pro Asp Asn
            420                 425                 430
Gly Glu Asp Lys Asn Tyr Arg Ser Leu Leu Cys Gly Asp Gly Phe Lys
            435                 440                 445
Ile Val Tyr Leu Pro Glu Ala Lys His Ile Arg His Leu Asp Leu Gln
            450                 455                 460
Asp Trp Asn Asn Thr Glu Asn Thr Ala Asp Glu Gln Lys Val Glu Phe
465                 470                 475                 480
Phe Gln Lys Ile Ile Lys Lys Leu Arg Val Asp Tyr Gln Pro Asn Leu
                485                 490                 495
Ile Asn Asp Pro Ser Leu Asp Ala Leu Gln Ala Asn Leu Leu Ala Leu
            500                 505                 510
Ser Leu Asp Phe Ser Thr Asp Thr Lys Gly Leu Asp Asn Leu Leu Asp
            515                 520                 525
Thr Ser Gln Gln Asp Lys Arg Ile Glu Lys Leu Leu Pro Asp Tyr Glu
530                 535                 540
Met Phe Ala Pro Glu Ala Pro Pro Lys Lys Arg Ala Ala Lys Ser
545                 550                 555                 560
Thr Thr Ala Gly Ala Ser Gly Pro Lys Met Ala Lys Ile Asp Asp Asp
                565                 570                 575
Gln Leu Lys Glu Phe Glu Phe Val Lys Ser Leu Asn Lys Asp Glu Ala
            580                 585                 590
Leu Thr Ser Cys Thr Ala Ala Gln Leu His Phe Ile Leu Gln His His
            595                 600                 605
Phe Asp Val Thr Met Pro Lys Ser Ser Lys Lys Ala Lys Leu Val Ala
610                 615                 620
Lys Ile Glu Glu Leu His Lys
625                 630

<210> SEQ ID NO 6
<211> LENGTH: 602
<212> TYPE: PRT
<213> ORGANISM: Saccharomyces cerevisiae

<400> SEQUENCE: 6

Met Arg Pro Val Thr Asn Ala Phe Gly Asn Ser Gly Glu Leu Asn Asp
  1               5                  10                  15
```

```
Gln Val Asp Glu Lys Gly Tyr Arg Lys Phe Asp Ile His Glu Gly Ile
             20                  25                  30

Leu Phe Cys Ile Glu Leu Ser Glu Thr Met Phe Lys Glu Ser Ser Asp
         35                  40                  45

Leu Asp Tyr Lys Ser Pro Leu Leu Glu Ile Leu Glu Ser Leu Asp Glu
     50                  55                  60

Leu Met Ser Gln Leu Val Ile Thr Arg Pro Gly Thr Ala Ile Gly Cys
 65                  70                  75                  80

Tyr Phe Tyr Tyr Cys Asn Arg Glu Asp Ala Lys Glu Gly Ile Tyr Glu
                 85                  90                  95

Leu Phe Pro Leu Arg Asp Ile Asn Ala Thr Phe Met Lys Lys Leu Asn
             100                 105                 110

Asp Leu Leu Glu Asp Leu Ser Ser Gly Arg Ile Ser Leu Tyr Asp Tyr
         115                 120                 125

Phe Met Phe Gln Gln Thr Gly Ser Glu Lys Gln Val Arg Leu Ser Val
     130                 135                 140

Leu Phe Thr Phe Met Leu Asp Thr Phe Leu Glu Glu Ile Pro Gly Gln
145                 150                 155                 160

Lys Gln Leu Ser Asn Lys Arg Val Phe Leu Phe Thr Asp Ile Asp Lys
                165                 170                 175

Pro Gln Glu Ala Gln Asp Ile Asp Glu Arg Ala Arg Leu Arg Arg Leu
            180                 185                 190

Thr Ile Asp Leu Phe Asp Asn Lys Val Asn Phe Ala Thr Phe Phe Ile
        195                 200                 205

Gly Tyr Ala Asp Lys Pro Phe Asp Asn Glu Phe Tyr Ser Asp Ile Leu
    210                 215                 220

Gln Leu Gly Ser His Thr Asn Glu Asn Thr Gly Leu Asp Ser Glu Phe
225                 230                 235                 240

Asp Gly Pro Ser Thr Lys Pro Ile Asp Ala Lys Tyr Ile Lys Ser Arg
                245                 250                 255

Ile Leu Arg Lys Lys Glu Val Lys Arg Ile Met Phe Gln Cys Pro Leu
            260                 265                 270

Ile Leu Asp Glu Lys Thr Asn Phe Ile Val Gly Val Lys Gly Tyr Thr
        275                 280                 285

Met Tyr Thr His Glu Lys Ala Gly Val Arg Tyr Lys Leu Val Tyr Glu
    290                 295                 300

His Glu Asp Ile Arg Gln Glu Ala Tyr Ser Lys Arg Lys Phe Leu Asn
305                 310                 315                 320

Pro Ile Thr Gly Glu Asp Val Thr Gly Lys Thr Val Lys Val Tyr Pro
                325                 330                 335

Tyr Gly Asp Leu Asp Ile Asn Leu Ser Asp Ser Gln Asp Gln Ile Val
            340                 345                 350

Met Glu Ala Tyr Thr Gln Lys Asp Ala Phe Leu Lys Ile Ile Gly Phe
        355                 360                 365

Arg Ser Ser Lys Ser Ile His Tyr Phe Asn Asn Ile Asp Lys Ser
    370                 375                 380

Ser Phe Ile Val Pro Asp Glu Ala Lys Tyr Glu Gly Ser Ile Arg Thr
385                 390                 395                 400

Leu Ala Ser Leu Leu Lys Ile Leu Arg Lys Lys Asp Lys Ile Ala Ile
                405                 410                 415

Leu Trp Gly Lys Leu Lys Ser Asn Ser His Pro Ser Leu Tyr Thr Leu
            420                 425                 430

Ser Pro Ser Ser Val Lys Asp Tyr Asn Glu Gly Phe Tyr Leu Tyr Arg
```

-continued

```
              435                 440                 445
Val Pro Phe Leu Asp Glu Ile Arg Lys Phe Pro Ser Leu Leu Ser Tyr
450                 455                 460

Asp Asp Gly Ser Glu His Lys Leu Asp Tyr Asp Asn Met Lys Val
465                 470                 475                 480

Thr Gln Ser Ile Met Gly Tyr Phe Asn Leu Arg Asp Gly Tyr Asn Pro
                485                 490                 495

Ser Asp Phe Lys Asn Pro Leu Leu Gln Lys His Tyr Lys Val Leu His
                500                 505                 510

Asp Tyr Leu Leu Gln Ile Glu Thr Thr Phe Asp Glu Asn Glu Thr Pro
        515                 520                 525

Asn Thr Lys Lys Asp Arg Met Met Arg Glu Asp Asp Ser Leu Arg Lys
530                 535                 540

Leu Tyr Tyr Ile Arg Asn Lys Ile Leu Glu Ser Glu Lys Ser Glu Asp
545                 550                 555                 560

Pro Thr Ile Gln Arg Leu Asn Lys Tyr Val Lys Ile Trp Asn Met Phe
                565                 570                 575

Tyr Lys Lys Phe Asn Asp Asp Asn Ile Ser Ile Lys Glu Glu Lys Lys
                580                 585                 590

Pro Phe Asp Lys Lys Pro Lys Phe Asn Ile
            595                 600

<210> SEQ ID NO 7
<211> LENGTH: 732
<212> TYPE: PRT
<213> ORGANISM: Homo sapiens

<400> SEQUENCE: 7

Met Val Arg Ser Gly Asn Lys Ala Ala Val Leu Cys Met Asp Val
1               5                   10                  15

Gly Phe Thr Met Ser Asn Ser Ile Pro Gly Ile Glu Ser Pro Phe Glu
            20                  25                  30

Gln Ala Lys Lys Val Ile Thr Met Phe Val Gln Arg Gln Val Phe Ala
        35                  40                  45

Glu Asn Lys Asp Glu Ile Ala Leu Val Leu Phe Gly Thr Asp Gly Thr
    50                  55                  60

Asp Asn Pro Leu Ser Gly Gly Asp Gln Tyr Gln Asn Ile Thr Val His
65                  70                  75                  80

Arg His Leu Met Leu Pro Asp Phe Asp Leu Leu Glu Asp Ile Glu Ser
                85                  90                  95

Lys Ile Gln Pro Gly Ser Gln Gln Ala Asp Phe Leu Asp Ala Leu Ile
            100                 105                 110

Val Ser Met Asp Val Ile Gln His Glu Thr Ile Gly Lys Lys Phe Glu
        115                 120                 125

Lys Arg His Ile Glu Ile Phe Thr Asp Leu Ser Ser Arg Phe Ser Lys
    130                 135                 140

Ser Gln Leu Asp Ile Ile His Ser Leu Lys Lys Cys Asp Ile Ser
145                 150                 155                 160

Leu Gln Phe Phe Leu Pro Phe Ser Leu Gly Lys Glu Asp Gly Ser Gly
                165                 170                 175

Asp Arg Gly Asp Gly Pro Phe Arg Leu Gly Gly His Gly Pro Ser Phe
            180                 185                 190

Pro Leu Lys Gly Ile Thr Glu Gln Gln Lys Glu Gly Leu Glu Ile Val
        195                 200                 205
```

-continued

```
Lys Met Val Met Ile Ser Leu Glu Gly Glu Asp Gly Leu Asp Glu Ile
210                 215                 220
Tyr Ser Phe Ser Glu Ser Leu Arg Lys Leu Cys Val Phe Lys Lys Ile
225                 230                 235                 240
Glu Arg His Ser Ile His Trp Pro Cys Arg Leu Thr Ile Gly Ser Asn
                245                 250                 255
Leu Ser Ile Arg Ile Ala Ala Tyr Lys Ser Ile Leu Gln Glu Arg Val
            260                 265                 270
Lys Lys Thr Trp Thr Val Asp Ala Lys Thr Leu Lys Lys Glu Asp
        275                 280                 285
Ile Gln Lys Glu Thr Val Tyr Cys Leu Asn Asp Asp Glu Thr Glu
    290                 295                 300
Val Leu Lys Glu Asp Ile Ile Gln Gly Phe Arg Tyr Gly Ser Asp Ile
305                 310                 315                 320
Val Pro Phe Ser Lys Val Asp Glu Glu Gln Met Lys Tyr Lys Ser Glu
                325                 330                 335
Gly Lys Cys Phe Ser Val Leu Gly Phe Cys Lys Ser Ser Gln Val Gln
                340                 345                 350
Arg Arg Phe Phe Met Gly Asn Gln Val Leu Lys Val Phe Ala Ala Arg
            355                 360                 365
Asp Asp Glu Ala Ala Ala Val Ala Leu Ser Ser Leu Ile His Ala Leu
370                 375                 380
Asp Asp Leu Asp Met Val Ala Ile Val Arg Tyr Ala Tyr Asp Lys Arg
385                 390                 395                 400
Ala Asn Pro Gln Val Gly Val Ala Phe Pro His Ile Lys His Asn Tyr
                405                 410                 415
Glu Cys Leu Val Tyr Val Gln Leu Pro Phe Met Glu Asp Leu Arg Gln
            420                 425                 430
Tyr Met Phe Ser Ser Leu Lys Asn Ser Lys Lys Tyr Ala Pro Thr Glu
        435                 440                 445
Ala Gln Leu Asn Ala Val Asp Ala Leu Ile Asp Ser Met Ser Leu Ala
    450                 455                 460
Lys Lys Asp Glu Lys Thr Asp Thr Leu Glu Asp Leu Phe Pro Thr Thr
465                 470                 475                 480
Lys Ile Pro Asn Pro Arg Phe Gln Arg Leu Phe Gln Cys Leu Leu His
                485                 490                 495
Arg Ala Leu His Pro Arg Glu Pro Leu Pro Ile Gln Gln His Ile
            500                 505                 510
Trp Asn Met Leu Asn Pro Pro Ala Glu Val Thr Thr Lys Ser Gln Ile
        515                 520                 525
Pro Leu Ser Lys Ile Lys Thr Leu Phe Pro Leu Ile Glu Ala Lys Lys
    530                 535                 540
Lys Asp Gln Val Thr Ala Gln Glu Ile Phe Gln Asp Asn His Glu Asp
545                 550                 555                 560
Gly Pro Thr Ala Lys Lys Leu Lys Thr Glu Gln Gly Gly Ala His Phe
                565                 570                 575
Ser Val Ser Ser Leu Ala Glu Gly Ser Val Thr Ser Val Gly Ser Val
            580                 585                 590
Asn Pro Ala Glu Asn Phe Arg Val Leu Val Lys Gln Lys Ala Ser
        595                 600                 605
Phe Glu Glu Ala Ser Asn Gln Leu Ile Asn His Ile Glu Gln Phe Leu
    610                 615                 620
Asp Thr Asn Glu Thr Pro Tyr Phe Met Lys Ser Ile Asp Cys Ile Arg
```

-continued

```
                625                 630                 635                 640
Ala Phe Arg Glu Glu Ala Ile Lys Phe Ser Glu Glu Gln Arg Phe Asn
                    645                 650                 655

Asn Phe Leu Lys Ala Leu Gln Glu Lys Val Glu Ile Lys Gln Leu Asn
                660                 665                 670

His Phe Trp Glu Ile Val Val Gln Asp Gly Ile Thr Leu Ile Thr Lys
                675                 680                 685

Glu Glu Ala Ser Gly Ser Ser Val Thr Ala Glu Glu Ala Lys Lys Phe
                690                 695                 700

Leu Ala Pro Lys Asp Lys Pro Ser Gly Asp Thr Ala Ala Val Phe Glu
705                 710                 715                 720

Glu Gly Gly Asp Val Asp Asp Leu Leu Asp Met Ile
                    725                 730

<210> SEQ ID NO 8
<211> LENGTH: 728
<212> TYPE: PRT
<213> ORGANISM: Caenorhabditis elegans

<400> SEQUENCE: 8

Met Pro Pro Lys Lys Val Ser Pro Gly Ile Thr Val Ile Leu Ile Asp
  1               5                  10                  15

Ala Gly Ser Asn Met Ser Val Lys Asp Thr Glu Thr Gly Lys Ser Ala
                 20                  25                  30

Phe Glu Asn Ala Ile Asn Ala Ala Asp Trp Ile Val Ser Arg Lys Leu
             35                  40                  45

Phe Ser Lys Asp Pro Glu Leu Phe Ser Val Met Ala Tyr Asn Leu Asp
         50                  55                  60

Pro Lys Glu Tyr Lys Thr Glu Val Gly Gly Gln Thr Phe Asn Gly Val
 65                  70                  75                  80

Gln Cys Gln Asn Glu Lys Phe Thr Pro Ala Ser Phe Asp His Leu Lys
                 85                  90                  95

Phe Ile Thr Lys Glu Leu Gln Gln Asn Thr Glu Met Ile Asp Pro Asn
            100                 105                 110

Phe Phe Lys Gly Val Leu Gly Ala Val Ala Val Leu Lys Asp Gln Ile
        115                 120                 125

Glu Ser Tyr Pro Asn Pro Ser Gly Ile Thr Leu Ile Val Leu Thr Asn
    130                 135                 140

Gly Leu Asn Glu Asn Ile Arg Gln Glu Asn Phe Asp Leu Leu Val Glu
145                 150                 155                 160

Ala Val Ser Glu Ser Asn Ala Asp Leu Met Ile Ile Gly Ile Asp Glu
                165                 170                 175

Asn Pro Glu Tyr Pro Ala Ser Arg Val Ala Glu Leu Ala Glu Thr Leu
            180                 185                 190

Glu Gly Arg Thr Tyr Thr Phe Gln Asn Val Ala Lys Met Leu Ser Thr
        195                 200                 205

Phe Gln Ala Arg Gln Lys Ser Glu Arg Lys Tyr Asn Lys Met Trp Asp
    210                 215                 220

Ile Ala Pro Gly Ile His Leu Pro Val Ile Phe Ala Leu Lys Ser Glu
225                 230                 235                 240

Lys Ser Thr Ala Leu Leu Lys Phe Lys Asn Ala Asp Ser Glu Gly Asn
                245                 250                 255

Glu Met Val Arg Leu Glu Gln Met His Val Glu Thr Asp Glu Val Ala
            260                 265                 270
```

```
Pro Lys Asp Glu Phe Lys Ser Pro Val Leu Glu Glu Lys Pro Lys Phe
    275                 280                 285

Gln Lys Asn Phe Lys Pro Val Glu Asn Ile Lys Thr Met His Gly Ser
    290                 295                 300

Glu Ile Leu Asn Phe Leu Lys Ser Ile Ile Asn Ala Ser Gly Tyr Asn
305                 310                 315                 320

Phe Gly Lys Ser Val Ile Met Met Asp Pro Glu Tyr Leu Lys Glu Lys
                325                 330                 335

Tyr Asn Asp His Asn Phe Asn Glu Gly Gln Thr Gly Gly Val Leu Lys
            340                 345                 350

Leu Ile Gln Phe Thr Lys Arg Ala Asn Ile Leu Asp Ser Tyr Leu Leu
        355                 360                 365

Asp Ala Ser Ala Lys Thr Val Leu Pro Ala Leu Asn Ser Pro Lys Ser
370                 375                 380

Gly Ala Thr Lys Ala Thr Val Ser Leu Ile Glu Ala Met Leu Ser Leu
385                 390                 395                 400

Arg Val Ala Ala Ile Cys Arg Tyr Thr Phe His Ala Lys Ser His Val
                405                 410                 415

Gln Leu Ile Ala Leu Leu Pro His Gln Asp Glu Glu Thr Gly Val Phe
            420                 425                 430

Tyr Leu Arg Ser Val Lys Leu Pro Phe Ser Asp Asp Met Arg Thr Leu
        435                 440                 445

Lys Phe Pro Lys Phe Ser Phe Asp Glu Glu Asp Glu Asp Leu Asn Lys
    450                 455                 460

Pro Thr Val Ala Gln Leu Ser Ala Val Asp Asp Leu Ile Asp Cys Met
465                 470                 475                 480

Gln Leu Gln Glu Asp Glu Ile Ser Ser Leu Val Glu Gly Gly Met Ser
                485                 490                 495

Asp Pro Lys Leu Gln Met Gln Cys His Phe Leu Lys Ser Leu Val Leu
            500                 505                 510

His Pro Asn Asp Thr Phe Glu Asn His Ser Asn Arg Thr Asn Gln Ile
        515                 520                 525

Leu Asp Gln Ile Met Ala Pro Lys Arg Arg Val Glu Ala Glu His Pro
    530                 535                 540

Glu Ile Phe Gln Lys Leu Gly Arg Glu Phe Asn Leu Gln Pro Ile Gln
545                 550                 555                 560

Lys Thr Lys Arg Glu Arg Val Thr Val Glu Pro Glu Asp Leu Gln Thr
                565                 570                 575

Met Ile Ser Glu Trp Thr Glu Lys Lys Gln Asn Met Thr Gln Pro Asp
            580                 585                 590

Glu Val Asp Asp Gly Ala Ser Gln Lys Lys Lys Lys Pro Asn Ala
        595                 600                 605

Lys Lys Leu Thr Arg Lys Glu Glu Val Gln Met Asp Ile Met Glu Asp
    610                 615                 620

Gly Gly Ala Ser Arg Val Cys Ser Lys Ile Leu Glu Met Ile Ser Asn
625                 630                 635                 640

Thr Cys Lys Phe Gln Pro Asn Gly Ala Val Thr Glu Phe Phe Thr Leu
                645                 650                 655

Leu Val Asn Glu Leu Asn Val Ile Arg Ser Val Phe Val Glu Asn Ser
            660                 665                 670

Lys Cys Asp Glu Phe Asn Glu Leu Leu Lys Lys Leu Lys Asp Glu Glu
        675                 680                 685

Asp Phe Glu Pro Phe Ala Glu Val Leu Ser Glu Glu Lys Ser Cys Asn
```

-continued

```
                690             695             700
Pro Ile Asp Ser Ser Glu Val Ser Met Ser Glu Val Ser Val Ala Asn
705                     710                     715                     720

Ala Ala Glu Phe Trp Glu Glu Asp
                725

<210> SEQ ID NO 9
<211> LENGTH: 629
<212> TYPE: PRT
<213> ORGANISM: Saccharomyces cerevisiae

<400> SEQUENCE: 9

Met Ser Ser Glu Ser Thr Thr Phe Ile Val Asp Val Ser Pro Ser Met
1               5                   10                  15

Met Lys Asn Asn Val Ser Lys Ser Met Ala Tyr Leu Glu Tyr Thr
                20                  25                  30

Leu Leu Asn Lys Ser Lys Lys Ser Arg Lys Thr Asp Trp Ile Ser Cys
            35                  40                  45

Tyr Leu Ala Asn Cys Pro Val Ser Glu Asn Ser Gln Glu Ile Pro Asn
        50                  55                  60

Val Phe Gln Ile Gln Ser Phe Leu Ala Pro Val Thr Thr Thr Ala Thr
65                  70                  75                  80

Ile Gly Phe Ile Lys Arg Leu Lys Gln Tyr Cys Asp Gln His Ser His
                85                  90                  95

Asp Ser Ser Asn Glu Gly Leu Gln Ser Met Ile Gln Cys Leu Leu Val
            100                 105                 110

Val Ser Leu Asp Ile Lys Gln Gln Phe Gln Ala Arg Lys Ile Leu Lys
        115                 120                 125

Gln Ile Val Val Phe Thr Asp Asn Leu Asp Asp Leu Asp Ile Thr Asp
130                 135                 140

Glu Glu Ile Asp Leu Leu Thr Glu Glu Leu Ser Thr Arg Ile Ile Leu
145                 150                 155                 160

Ile Asp Cys Gly Lys Asp Thr Gln Glu Glu Arg Lys Lys Ser Asn Trp
                165                 170                 175

Leu Lys Leu Val Glu Ala Ile Pro Asn Ser Arg Ile Tyr Asn Met Asn
            180                 185                 190

Glu Leu Leu Val Glu Ile Thr Ser Pro Ala Thr Ser Val Val Lys Pro
        195                 200                 205

Val Arg Val Phe Ser Gly Glu Leu Arg Leu Gly Ala Asp Ile Leu Ser
210                 215                 220

Thr Gln Thr Ser Asn Pro Ser Gly Ser Met Gln Asp Glu Asn Cys Leu
225                 230                 235                 240

Cys Ile Lys Val Glu Ala Phe Pro Ala Thr Lys Ala Val Ser Gly Leu
                245                 250                 255

Asn Arg Lys Thr Ala Val Glu Val Glu Asp Ser Gln Lys Lys Glu Arg
            260                 265                 270

Tyr Val Gly Val Lys Ser Ile Ile Glu Tyr Glu Ile His Asn Glu Gly
        275                 280                 285

Asn Lys Lys Asn Val Ser Glu Asp Gln Ser Gly Ser Ser Tyr Ile
290                 295                 300

Pro Val Thr Ile Ser Lys Asp Ser Val Thr Lys Ala Tyr Arg Tyr Gly
305                 310                 315                 320

Ala Asp Tyr Val Val Leu Pro Ser Val Leu Val Asp Gln Thr Val Tyr
                325                 330                 335
```

```
Glu Ser Phe Pro Gly Leu Asp Leu Arg Gly Phe Leu Asn Arg Glu Ala
                340                 345                 350

Leu Pro Arg Tyr Phe Leu Thr Ser Glu Ser Phe Ile Thr Ala Asp
        355                 360                 365

Thr Arg Leu Gly Cys Gln Ser Asp Leu Met Ala Phe Ser Ala Leu Val
        370                 375                 380

Asp Val Met Leu Glu Asn Arg Lys Ile Ala Val Ala Arg Tyr Val Ser
385                 390                 395                 400

Lys Lys Asp Ser Glu Val Asn Met Cys Ala Leu Cys Pro Val Leu Ile
                405                 410                 415

Glu His Ser Asn Ile Asn Ser Glu Lys Lys Phe Val Lys Ser Leu Thr
                420                 425                 430

Leu Cys Arg Leu Pro Phe Ala Glu Asp Glu Arg Val Thr Asp Phe Pro
                435                 440                 445

Lys Leu Leu Asp Arg Thr Thr Thr Ser Gly Val Pro Leu Lys Lys Glu
450                 455                 460

Thr Asp Gly His Gln Ile Asp Glu Leu Met Glu Gln Phe Val Asp Ser
465                 470                 475                 480

Met Asp Thr Asp Glu Leu Pro Glu Ile Pro Leu Gly Asn Tyr Tyr Gln
                485                 490                 495

Pro Ile Gly Glu Val Thr Thr Asp Thr Thr Leu Pro Leu Pro Ser Leu
                500                 505                 510

Asn Lys Asp Gln Glu Glu Asn Lys Lys Asp Pro Leu Arg Ile Pro Thr
                515                 520                 525

Val Phe Val Tyr Arg Gln Gln Gln Val Leu Leu Glu Trp Ile His Gln
530                 535                 540

Leu Met Ile Asn Asp Ser Arg Glu Phe Glu Ile Pro Glu Leu Pro Asp
545                 550                 555                 560

Ser Leu Lys Asn Lys Ile Ser Pro Tyr Thr His Lys Lys Phe Asp Ser
                565                 570                 575

Thr Lys Leu Val Glu Val Leu Gly Ile Lys Lys Val Asp Lys Leu Lys
                580                 585                 590

Leu Asp Ser Glu Leu Lys Thr Glu Leu Glu Arg Glu Lys Ile Pro Asp
                595                 600                 605

Leu Glu Thr Leu Leu Lys Arg Gly Glu Gln His Ser Arg Gly Ser Pro
        610                 615                 620

Asn Ser Asn Asn
625

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Linker

<400> SEQUENCE: 10

Ser Gly Ser Gly
 1

<210> SEQ ID NO 11
<211> LENGTH: 34
<212> TYPE: PRT
<213> ORGANISM: Homo sapiens

<400> SEQUENCE: 11

Glu Glu Ala Lys Lys Phe Leu Ala Pro Lys Asp Lys Pro Ser Gly Asp
```

-continued

```
                1               5                  10                     15
Thr Ala Ala Val Phe Glu Glu Gly Gly Asp Val Asp Asp Leu Leu Asp
                        20                  25                 30

Met Ile

<210> SEQ ID NO 12
<211> LENGTH: 12
<212> TYPE: PRT
<213> ORGANISM: Homo sapiens

<400> SEQUENCE: 12

Glu Glu Ala Lys Lys Phe Leu Ala Pro Lys Asp Lys
  1               5                  10

<210> SEQ ID NO 13
<211> LENGTH: 12
<212> TYPE: PRT
<213> ORGANISM: Homo sapiens

<400> SEQUENCE: 13

Leu Ala Pro Lys Asp Lys Pro Ser Gly Asp Thr Ala
  1               5                  10

<210> SEQ ID NO 14
<211> LENGTH: 12
<212> TYPE: PRT
<213> ORGANISM: Homo sapiens

<400> SEQUENCE: 14

Pro Ser Gly Asp Thr Ala Ala Val Phe Glu Glu Gly
  1               5                  10

<210> SEQ ID NO 15
<211> LENGTH: 12
<212> TYPE: PRT
<213> ORGANISM: Homo sapiens

<400> SEQUENCE: 15

Ala Val Phe Glu Glu Gly Gly Asp Val Asp Asp Leu
  1               5                  10

<210> SEQ ID NO 16
<211> LENGTH: 78
<212> TYPE: PRT
<213> ORGANISM: Homo sapiens

<400> SEQUENCE: 16

Phe Asn Asn Phe Leu Lys Ala Leu Gln Glu Lys Val Glu Ile Lys Gln
  1               5                  10                     15

Leu Asn His Phe Trp Glu Ile Val Val Gln Asp Gly Ile Thr Leu Ile
                        20                  25                 30

Thr Lys Glu Glu Ala Ser Gly Ser Ser Val Thr Ala Glu Glu Ala Lys
                35                  40                  45

Lys Phe Leu Ala Pro Lys Asp Lys Pro Ser Gly Asp Thr Ala Ala Val
            50                  55                  60

Phe Glu Glu Gly Gly Asp Val Asp Asp Leu Leu Asp Met Ile
 65                  70                  75

<210> SEQ ID NO 17
<211> LENGTH: 77
<212> TYPE: PRT
<213> ORGANISM: Cricetulus griseus
```

-continued

```
<400> SEQUENCE: 17

Phe Asn Ser Phe Leu Glu Ala Leu Arg Glu Lys Val Glu Ile Lys Gln
 1               5                  10                  15

Leu Asn His Phe Trp Glu Ile Val Val Gln Asp Gly Val Thr Leu Ile
                20                  25                  30

Thr Lys Asp Glu Gly Ser Gly Ser Ser Val Thr Thr Glu Glu Ala Thr
            35                  40                  45

Lys Phe Leu Ala Pro Lys Asp Lys Ala Lys Glu Asp Ala Ala Gly Leu
        50                  55                  60

Glu Glu Gly Gly Asp Val Asp Asp Leu Leu Asp Met Ile
65                  70                  75

<210> SEQ ID NO 18
<211> LENGTH: 77
<212> TYPE: PRT
<213> ORGANISM: Mus musculus

<400> SEQUENCE: 18

Phe Asn Ser Phe Leu Glu Ala Leu Arg Glu Lys Val Glu Ile Lys Gln
 1               5                  10                  15

Leu Asn His Phe Trp Glu Ile Val Val Gln Asp Gly Val Thr Leu Ile
                20                  25                  30

Thr Lys Asp Glu Ala Pro Gly Ser Ser Ile Thr Ala Glu Glu Ala Lys
            35                  40                  45

Lys Phe Leu Ala Pro Lys Asp Lys Ala Lys Glu Asp Thr Thr Gly Pro
        50                  55                  60

Glu Glu Ala Gly Asp Val Asp Asp Leu Leu Asp Met Ile
65                  70                  75
```